(12) United States Patent
Nagata

(10) Patent No.: US 11,840,709 B2
(45) Date of Patent: Dec. 12, 2023

(54) MITOCHONDRIA ISOLATION

(71) Applicant: Takako Nagata, Washington, DC (US)

(72) Inventor: Takako Nagata, Washington, DC (US)

( * ) Notice: Subject to any disclaimer, the term of this patent is extended or adjusted under 35 U.S.C. 154(b) by 145 days.

(21) Appl. No.: 17/226,333

(22) Filed: Apr. 9, 2021

(65) Prior Publication Data

US 2021/0317418 A1 Oct. 14, 2021

Related U.S. Application Data

(60) Provisional application No. 63/008,392, filed on Apr. 10, 2020.

(51) Int. Cl.
*C12N 1/02* (2006.01)
*C12N 5/16* (2006.01)

(52) U.S. Cl.
CPC .................... *C12N 5/16* (2013.01); *C12N 1/02* (2013.01)

(58) Field of Classification Search
CPC .............. C12N 5/16; C12N 1/02; C12N 1/06
See application file for complete search history.

(56) References Cited

FOREIGN PATENT DOCUMENTS

WO    WO 2009054994 A2 *   4/2009  ............. A61K 38/46

OTHER PUBLICATIONS

Ku H.S. et al., "Isolation of Active Mitochondria From Tomato Fruit", Plant Physiol., (1968), vol. 43, pp. 883-887. (Year: 1968).*
Tang B. et al., "Magnetic nanoparticles: An improved method for mitochondrial isolation", Molecular Medicine Reports, 2012, vol. 5, pp. 1271-1276. (Year: 2012).*
Clark et al., "GenBank," *Nucleic Acids Research*, 44(D1): D67-D72 (2016).
Green et al., "Molecular Cloning: a Laboratory Manual," 4th edition, Cold Spring Harbor, NY, (2012).
MacPherson et al., "PCR 2: A Practical Approach," IRL Press, Ithaca, NY (1995).
Quiros et al., "Analysis of mtDNA/nDNA ratio in mice," Current Protocols in Mouse Biology, 7:47-54 (2017).
Smith, "The past, present and future of mitochondrial genomics: have we sequenced enough mtDNAs?" *Briefings in Functional Genomics*, 15(1): 47-54 (2016).

* cited by examiner

*Primary Examiner* — Satyendra K Singh
(74) *Attorney, Agent, or Firm* — Arnold & Porter Kaye Scholer LLP

(57) ABSTRACT

The present disclosure relates to methods and compositions for isolating mitochondria from cells and tissues. The methods provided herein are suitable for use in plants, animals, and fungi.

17 Claims, 3 Drawing Sheets

Figure 1
Figure 1A
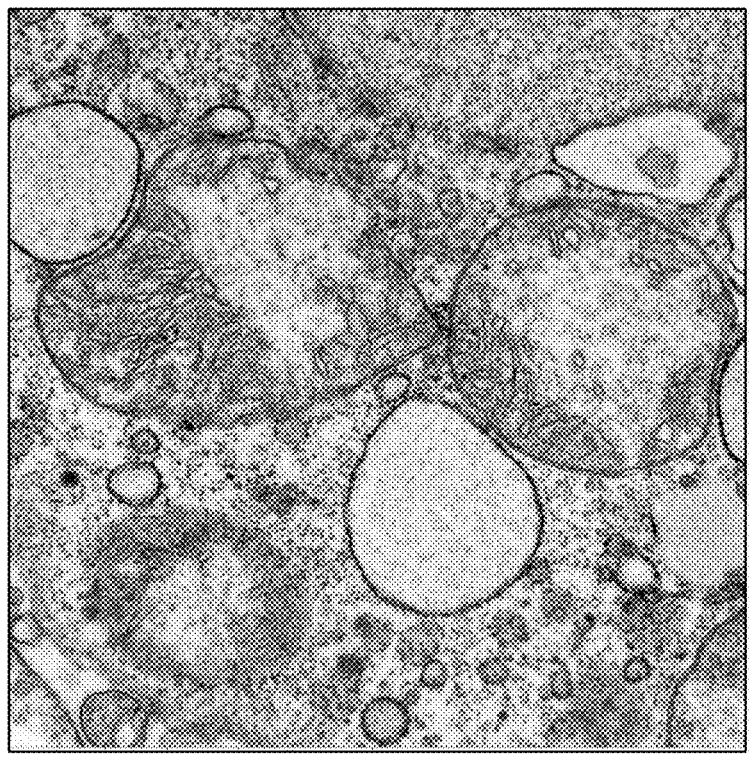
Figure 1B
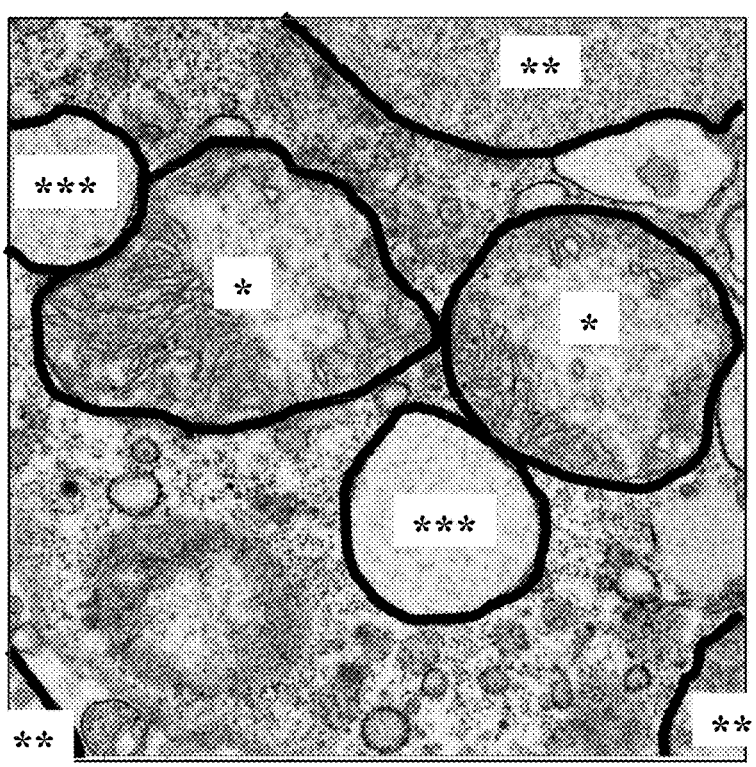

Figure 2
Figure 2A
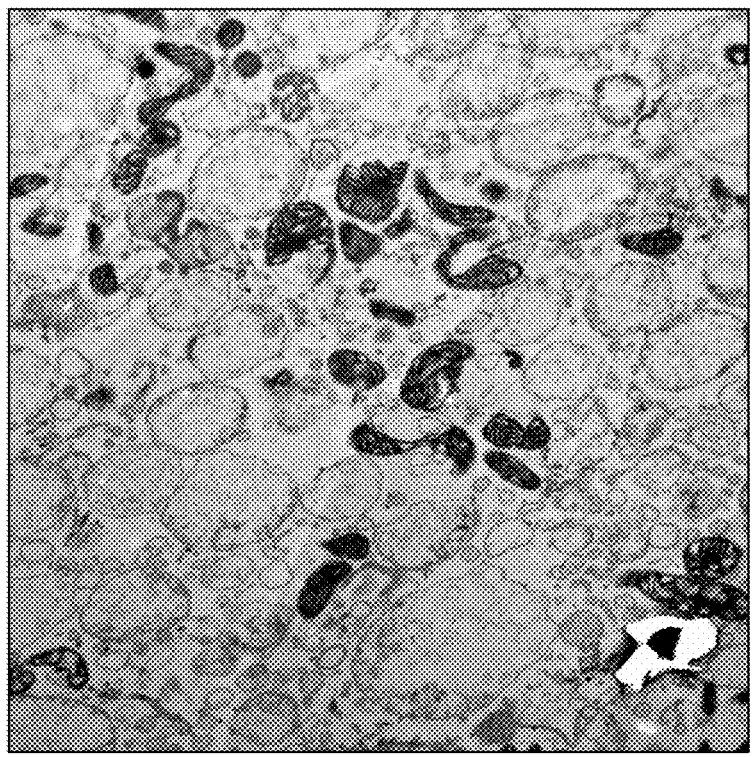
Figure 2B
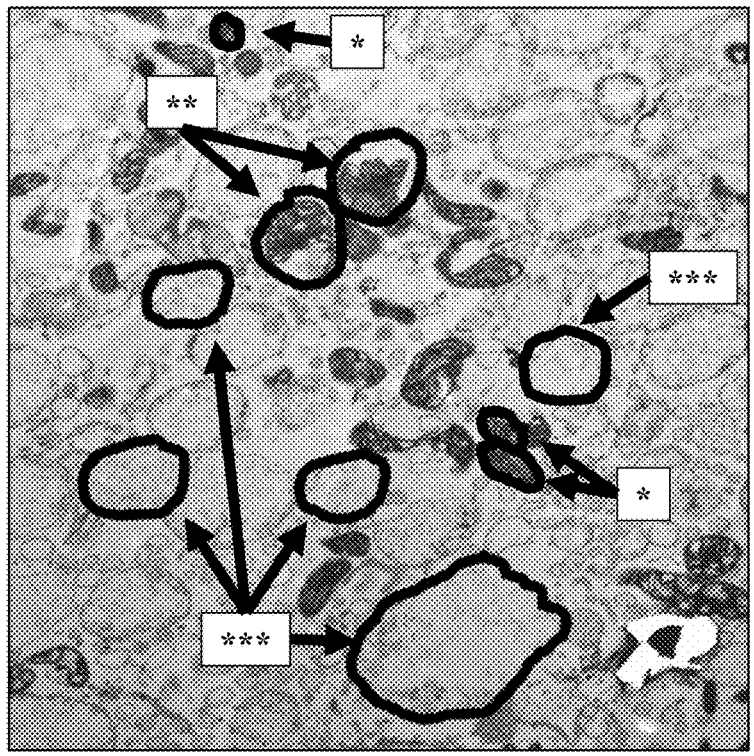

Figure 3
Figure 3A
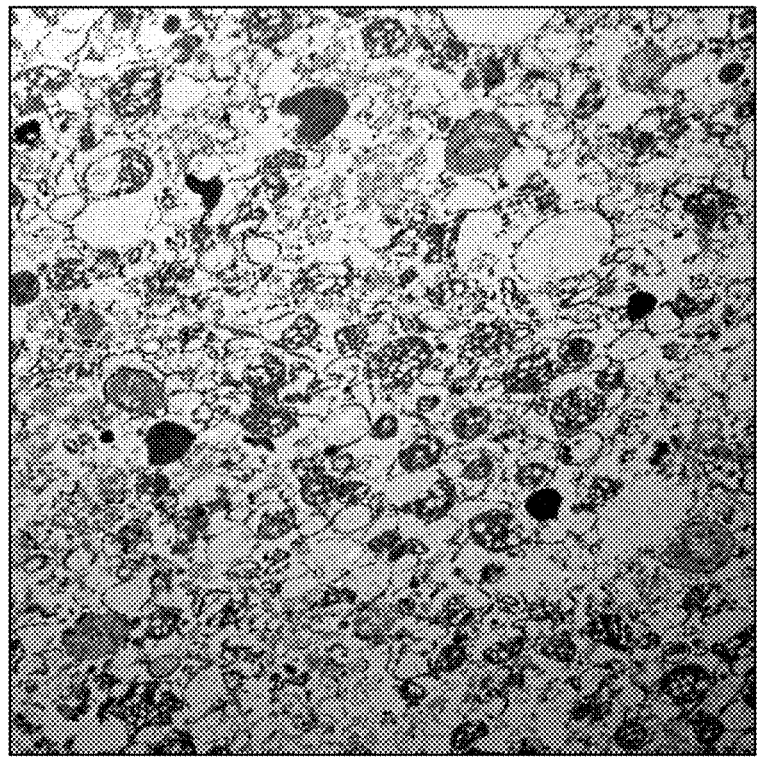
Figure 3B
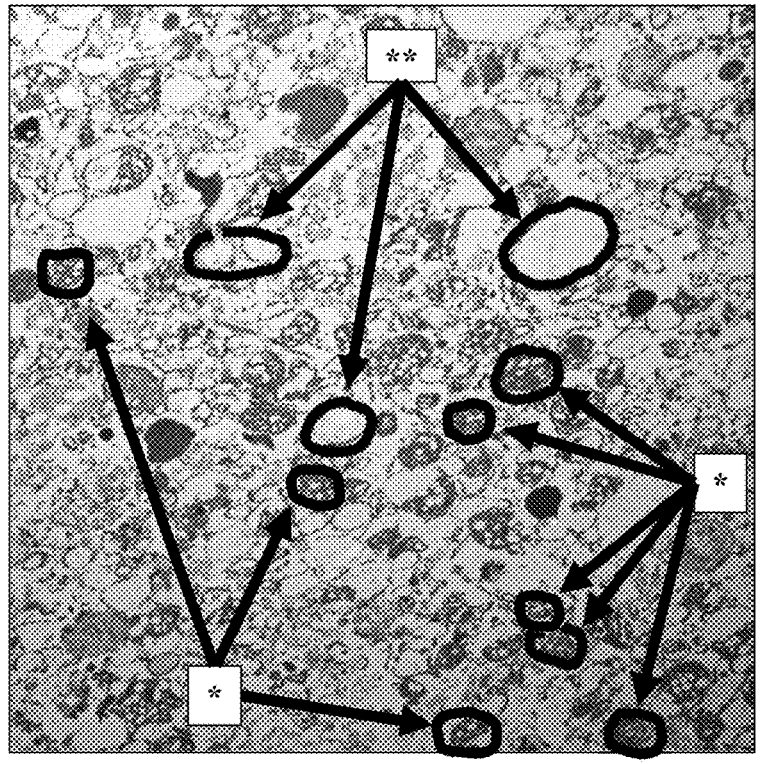

MITOCHONDRIA ISOLATION

CROSS-REFERENCE TO RELATED APPLICATION

This application claims the benefit of U.S. Provisional Application No. 63/008,392, filed Apr. 10, 2020, which is incorporated by reference in its entirety herein.

FIELD

The present disclosure relates to methods and compositions for isolating mitochondria from cells and tissues.

BACKGROUND

Mitochondria are double membrane-bound organelles found in most eukaryotic organisms, including animals, plants, and fungi. Mitochondria comprise their own genomes, independent from nuclear genomes, that give rise to unique mitochondrial proteins. Mitochondria have many functions, but their major function is to provide cells with energy via the production of adenosine triphosphate (ATP) through respiration.

Given their importance to the health of many eukaryotes, much effort has been expended to isolate intact mitochondria, mitochondrial proteins, and mitochondrial genomes. Typically, mitochondria isolation has been a laborious process involving dounce homogenization. The art has a need for a fast, reliable, isolation protocol that yields very pure mitochondria samples for downstream experimentation.

SUMMARY

In one aspect, this disclosure provides a method for isolated intact mitochondria from a population of cells comprising: (a) suspending the population of cells in a buffer comprising: (i) sucrose; (ii) magnesium chloride ($MgCl_2$); and (iii) 2-Amino-2-(hydroxymethyl)-1,3-propanediol hydrochloride (Tris-HCl) to generate a cell suspension; (b) centrifuging the cell suspension to generate a supernatant; (c) centrifuging the supernatant to generate a first mitochondria-rich pellet; and (d) resuspending the first mitochondria-rich pellet in the buffer to generate a first mitochondrial suspension. In an aspect, the method further comprises: (e) centrifuging the first mitochondrial suspension to generate a second mitochondria-rich pellet; (f) resuspending the second mitochondria-rich pellet in the buffer to generate a second mitochondrial suspension; (g) centrifuging the second mitochondrial suspension to generate a third mitochondria-rich pellet; and (h) resuspending the third mitochondria-rich pellet in the buffer to generate a third mitochondrial suspension.

In one aspect, this disclosure provides a method for isolating intact mitochondria from a tissue comprising: (a) generating a mashed tissue; (b) suspending the mashed tissue in a buffer comprising: (i) sucrose; (ii) magnesium chloride ($MgCl_2$); and (iii) 2-Amino-2-(hydroxymethyl)-1,3-propanediol hydrochloride (Tris-HCl) to generate a cell suspension; (c) centrifuging the cell suspension to generate a supernatant; (d) centrifuging the supernatant to generate a first mitochondria-rich pellet; and (e) resuspending the first mitochondria-rich pellet in the buffer to generate a first mitochondrial suspension. In an aspect, the method further comprises (f) centrifuging the first mitochondrial suspension to generate a second mitochondria-rich pellet; (g) resuspending the second mitochondria-rich pellet in the buffer to generate a second mitochondrial suspension; (h) centrifuging the second mitochondrial suspension to generate a third mitochondria-rich pellet; and (i) resuspending the third mitochondria-rich pellet in the buffer to generate a third mitochondrial suspension.

In one aspect, this disclosure provides a kit for isolating intact mitochondria from a population of cells or a tissue comprising a buffer, where the buffer comprises about 250 mM sucrose, about 5 mM magnesium chloride, and about 10 mM 2-Amino-2-(hydroxymethyl)-1,3-propanediol hydrochloride (Tris-HCl) (pH.7.4).

BRIEF DESCRIPTION OF THE DRAWINGS

FIG. 1 comprises FIG. 1A and FIG. 1B. FIG. 1A is a transmission electron micrograph of a mitochondrial fraction isolated using Kit T. Almost no intact mitochondria are observed. FIG. 1B is a labeled version of the micrograph depicted in FIG. 1A. (*) labels broken and swollen mitochondria that retain only their outer membrane and no cristae. () labels contamination with broken nuclei. (*) labels contamination with swollen rough endoplasmic reticulum.

FIG. 2 comprises FIG. 2A and FIG. 2B. FIG. 2A is a transmission electron micrograph of a mitochondrial fraction isolated using Kit Q. FIG. 2B is a labeled version of the micrograph depicted in FIG. 2A. (*) labels intact mitochondria. () labels broken mitochondria. (*) labels contamination with swollen rough endoplasmic reticulum.

FIG. 3 comprises FIG. 3A and FIG. 3B. FIG. 3A is a transmission electron micrograph of a mitochondrial fraction isolated using mitochondria isolation methods provided herein. FIG. 3B is a labeled version of the micrograph depicted in FIG. 3A. (*) labels intact mitochondria. (**) labels contamination with swollen rough endoplasmic reticulum.

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of this disclosure includes, unless otherwise indicated, conventional techniques of biochemistry, chemistry, molecular biology, microbiology, cell biology, plant biology, animal biology, biotechnology, and genetics, which are within the skill of the art. See, for example, Green and Sambrook, Molecular Cloning: A Laboratory Manual, 4th edition (2012); Current Protocols In Molecular Biology (F.

M. Ausubel, et al. eds., (1987)); Plant Breeding Methodology (N. F. Jensen, Wiley-Interscience (1988)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc.

As used herein, terms in the singular and the singular forms "a," "an," and "the," for example, include plural referents unless the content clearly dictates otherwise.

As used herein, the term "about," in conjunction with a number, refers to plus-or-minus 10% of the number. For example, "about 100" refers to the range of 90 (e.g., 100 minus 10%) to 110 (e.g., 100 plus 10%).

When a range is given, e.g., between 1 and 10, the whole numbers at the end of the range (e.g., 1 and 10) are to be included with every number between the ends of the range.

Any composition provided herein is envisioned for use with any method provided herein.

Mitochondria are double-membrane-bound organelles found in most eukaryotic cells, including those of animals, plants, and fungi. Up to several thousand mitochondria can be found in a single cell, with numbers varying widely based on cell type and organism type. Mitochondria are often referred to as the "powerhouse" of a cell, as they generate most of the cell's adenosine triphosphate (ATP) via respiration. Mitochondria also play an important role in controlling the concentration of calcium ($Ca^{2+}$) ions within a cell.

Unlike most organelles, mitochondria comprise their own DNA-based genome (the "mitochondrial genome") that is separate and distinct from the nuclear genome of a cell. Several thousand mitochondrial genomes have been sequenced and are available online. See, for example, Smith, "The past, present and future of mitochondrial genomics: have we sequenced enough mtDNAs?," *Brief Funct. Genomics,* 15:47-54 (2016).

In most animals, the mitochondrial genome comprises a circular chromosome that consists of between about 11,000 nucleotides and about 28,000 nucleotides. The human mitochondrial genome comprises about 16,500 nucleotides, and it encodes 37 genes that are essential for normal mitochondrial function.

In contrast to animals, plants and fungi mitochondrial genomes can range in length from about 19,000 nucleotides to over 10,000,000 nucleotides, and the mitochondria chromosomes can be linear or circular in structure.

Given the important role of mitochondria to an organism, it is not surprising that failures or deficiencies in mitochondria can cause disease. Dozens of mitochondrial diseases have been identified in humans, although their incidence tends to be rare.

In order to be able to study mitochondria, and mitochondrial diseases, it is important to be able to isolate mitochondria from a desired cell or tissue type. However, many mitochondria isolation protocols can contain other, unwanted, cellular components such as nuclear DNA or plastids (e.g., chloroplasts). Here, a novel mitochondria isolation protocol is provided to quickly isolate high purity mitochondria samples.

In an aspect, this disclosure provides a method for isolated intact mitochondria from a population of cells comprising: (a) suspending the population of cells in a buffer comprising: (i) sucrose; (ii) magnesium chloride ($MgCl_2$); and (iii) 2-Amino-2-(hydroxymethyl)-1,3-propanediol hydrochloride (Tris-HCl) to generate a cell suspension; (b) centrifuging the cell suspension to generate a supernatant; (c) centrifuging the supernatant to generate a first mitochondria-rich pellet; and (d) resuspending the first mitochondria-rich pellet in the buffer to generate a first mitochondrial suspension. In an aspect, the method further comprises: (e) centrifuging the first mitochondrial suspension to generate a second mitochondria-rich pellet; (f) resuspending the second mitochondria-rich pellet in the buffer to generate a second mitochondrial suspension; (g) centrifuging the second mitochondrial suspension to generate a third mitochondria-rich pellet; and (h) resuspending the third mitochondria-rich pellet in the buffer to generate a third mitochondrial suspension.

As used herein, a "population of cells" refers to a group of one or more cells. In an aspect, a population of cells comprises a group of two or more cells. In another aspect, a population of cells comprises a group of 100 or more cells. In a further aspect, a population of cells comprises a group of 1000 or more cells. In another aspect, a population of cells comprises a group of 10,000 or more cells. In another aspect, a population of cells comprises a group of 100,000 or more cells. In another aspect, a population of cells comprises a group of 500,000 or more cells. In another aspect, a population of cells comprises a group of 1,000,000 or more cells. In another aspect, a population of cells comprises a group of 2,500,000 or more cells. In another aspect, a population of cells comprises a group of 5,000,000 or more cells. In another aspect, a population of cells comprises a group of 10,000,000 or more cells. In another aspect, a population of cells comprises a group of 25,000,000 or more cells. In another aspect, a population of cells comprises a group of 50,000,000 or more cells.

In an aspect, a population of cells comprises between 1 cell and 100,000,000 cells. In another aspect, a population of cells comprises between 1 cell and 50,000,000 cells. In another aspect, a population of cells comprises between 1 cell and 25,000,000 cells. In another aspect, a population of cells comprises between 1 cell and 10,000,000 cells. In another aspect, a population of cells comprises between 1 cell and 5,000,000 cells. In another aspect, a population of cells comprises between 1 cell and 2,500,000 cells. In another aspect, a population of cells comprises between 1 cell and 1,000,000 cells. In another aspect, a population of cells comprises between 1 cell and 500,000 cells. In another aspect, a population of cells comprises between 1 cell and 250,000 cells. In another aspect, a population of cells comprises between 1 cell and 100,000 cells. In another aspect, a population of cells comprises between 1 cell and 50,000 cells. In another aspect, a population of cells comprises between 1 cell and 25,000 cells. In another aspect, a population of cells comprises between 1 cell and 10,000 cells. In another aspect, a population of cells comprises between 1 cell and 5,000 cells. In another aspect, a population of cells comprises between 1 cell and 1,000 cells. In another aspect, a population of cells comprises between 1 cell and 500 cells. In another aspect, a population of cells comprises between 100 cells and 50,000,000 cells. In another aspect, a population of cells comprises between 1,000 cells and 50,000,000 cells. In another aspect, a population of cells comprises between 10,000 cells and 50,000,000 cells. In another aspect, a population of cells comprises between 100,000 cells and 50,000,000 cells.

In an aspect, a population of cells comprises cells from a single organism. In another aspect, a population of cells comprises cells from two or more organisms of the same species. In a further aspect, a population of cells comprises cells from two or more organisms of two or more different species.

In an aspect, a population of cells comprises cells from a single tissue. In another aspect, a population of cells comprises cells from two or more tissues.

In an aspect, a population of cells comprises a population of adherent cells. As used herein, "adherent" cells are grown as mono-layers on an artificial substrate (e.g., a flask, a petri dish). Adherent cells are also referred to as anchorage-dependent cells.

In an aspect, a population of cells comprises a population of non-adherent cells. As used herein, "non-adherent" cells are cells that are free-floating in a culture medium. Non-adherent cells are also referred to as suspension cells.

In an aspect, a population of cells comprises adherent cells and non-adherent cells.

In an aspect, a population of adherent cells is washed in phosphate buffered saline (PBS) prior to suspending the population of adherent cells in a buffer. PBS is typically used a concentration of 1× ("1× PBS"). At 1× concentration, PBS comprises 137 mM NaCl, 2.7 mM KCl, 10 mM $Na_2HPO_4$, and 1.8 mM $KH_2PO_4$. In an aspect, PBS comprises a concentration of 0.7×. In another aspect, PBS comprises a concentration of 0.8×. In another aspect, PBS comprises a concentration of 0.9×. In another aspect, PBS comprises a concentration of 1×. In another aspect, PBS comprises a concentration of 1.1×. In another aspect, PBS comprises a concentration of 1.2×. In another aspect, PBS comprises a concentration of 1.3×. In another aspect, PBS comprises a concentration of between 0.5x and 1.5×. In another aspect, PBS comprises a concentration of between 0.7x and 1.3×. In another aspect, PBS comprises a concentration of between 0.9× and 1.1×.

In an aspect, a population of cells is a population of transgenic cells. In an aspect, a population of cells comprises at least one transgenic cell. As used herein, a "transgenic cell" refers to a cell comprising a recombinant nucleic acid molecule or construct.

In an aspect, a population of cells is a population of somatic cells. In an aspect, a population of cells comprises at least one somatic cell. As used herein, a "somatic cell" refers to any non-reproductive cell of an organism (e.g., cells that do not give rise to gametes).

In an aspect, a population of cells is a population of germinal cells. In an aspect, a population of cells comprises at least one germinal cell. As used herein, a "germinal cell" refers to any cell that gives rise to the gametes of an organism.

In an aspect, a population of cells is a population of stem cells. In an aspect, a population of cells comprises at least one stem cell. As used herein, a "stem cell" refers to an unspecialized cell that can develop into one or more different cell types. In an aspect, a stem cell is an embryonic stem cell. In another aspect, a stem cell is an adult stem cell. In a further aspect, a stem cell is an induced pluripotent stem cell. Typically, stem cells require certain physiologic or experimental conditions in order to differentiate into specialized cells.

In an aspect, a population of cells is a population of cancer cells.

In an aspect, a population of cells is an isolated population of cells. As used herein, an "isolated population" of cells refers to one or more cells that have been grown in vitro or ex vivo.

As used herein, "primate" refers to any organism belonging to the order Primates. As used herein, "rodent" refers to any organism belonging to the order Rodentia. As used herein, "canine" refers to any organism belonging to the family Canidae. As used herein, "feline" refers to any organism belonging to the family Felidae. As used herein, "artiodactyl" refers to any organism belonging to the order Artiodactyla. As used herein, "lagomorph" refers to any organism belonging to the order Lagomorpha. As used herein, "marsupial" refers to any organism belonging to the infraclass Marsupialia. As used herein, "perissodactyl" refers to any organism belonging to the order Perissodactyla. As used herein, "plant" refers to any organism belonging to the group Viridiplantae. As used herein, "fungal" refers to any organism belonging to the Kingdom Fungi.

In an aspect, a population of cells is selected from the group consisting of a population of mammal cells, a population of fish cells, a population of reptile cells, a population of amphibian cells, a population of avian cells, a population of insect cells, a population of plant cells, and a population of fungal cells.

In an aspect, a population of mammal cells is selected from the group of a population of primate cells, a population of rodent cells, a population of canine cells, a population of feline cells, a population of artiodactyl cells, a population of lagomorph cells, a population of marsupial cells, and a population of perissodactyl cells.

In an aspect, a population of primate cells is selected from the group consisting of a population of human cells, a population of chimpanzee cells, a population of orangutan cells, a population of gorilla cells, a population of bonobo cells, and a population of lemur cells. In an aspect, human cells are *Homo sapiens* cells. In an aspect, chimpanzee cells are *Pan troglodytes* cells. In an aspect, orangutan cells are *Pongo pygmaeus* cells, *Pongo abelii* cells, or *Pongo tapanuliensis* cells. In an aspect, gorilla cells are *Gorilla gorilla* cells or *Gorilla beringei* cells. In an aspect, bonobo cells are *Pan paniscus* cells. In an aspect, lemur cells are superfamily Lemuroidea cells.

In an aspect, a population of rodent cells is selected from the group consisting of a population of mouse cells and a population of rat cells. In an aspect, a mouse cell is a *Mus musculus* cell. In an aspect, a mouse cell is a *Peromyscus leucopus* cell. In another aspect, a mouse cell is a *Peromyscus maniculatus* cell. In an aspect, a rat cell is a *Rattus norvegicus* cell. In another aspect, a rat cell is a *Rattus norvegicus* domestica cell.

In an aspect, a population of artiodactyl cells is selected from the group consisting of a population of cattle cells, a population of deer cells, a population of sheep cells, a population of pig cells, and a population of goat cells. In an aspect, a cattle cell is a *Bos taurus* cell. In an aspect, a deer cell is a family Cervidae cell. In another aspect, a deer cell is a *Cervus* cell. In another aspect, a deer cell is an *Odocoileus* cell. In another aspect, a deer cell is an *Alces* cell. In another aspect, a deer cell is a *Rangifer* cell. In an aspect, a sheep cell is an *Ovis aries* cell. In an aspect, a pig cell is a *Sus scrofa* cell. In another aspect, a pig cell is a *Sus scrofa domesticus* cell. In an aspect, a goat cell is a *Capra aegagrus* cell. In another aspect, a goat cell is a *Capra aegagrus* hircus cell.

In an aspect, a population of perissodactyl cells is a population of horse cells. In an aspect, a horse cell is an *Equus ferus* cell. In another aspect, a horse cell is an *Equus ferus caballus* cell.

In an aspect, a population of plant cells is selected from the group consisting of a population of *Arabidopsis* cells, a population of corn cells, a population of rice cells, a population of soybean cells, a population of wheat cells, a population of sorghum cells, a population of alfalfa cells, a population of *Triticale* cells, a population of tomato cells, a population of potato cells, a population of cucumber cells, a population of canola cells, a population of tobacco cells, a population of algae cells, and a population of *Selaginella* cells.

In an aspect, a plant cell is a gymnosperm cell. In an aspect, a plant cell is an angiosperm cell. In an aspect, a plant cell is a dicotyledonous cell. In an aspect, a plant cell is a monocotyledonous cell.

In an aspect, an *Arabidopsis* cell is an *Arabidopsis thaliana* cell. In an aspect, a corn cell is a *Zea mays* cell. In an aspect, a rice cell is an *Oryza sativa* cell or an *Oryza rufipogon* cell. In an aspect, a soybean cell is a *Glycine max* cell. In an aspect, a wheat cell is a *Triticum aestivum* cell, a *Triticum spelta* cell, or a *Triticum durum* cell. In an aspect, a sorghum cell is a *Sorghum bicolor* cell. In an aspect, an alfalfa cell is a *Medicago sativa* cell. In an aspect, a tomato cell is a *Solanum lycopersicum* cell. In an aspect, a potato cell is a *Solanum tuberosum* cell. In an aspect, a cucumber cell is a *Cucumis sativus* cell. In an aspect, a canola cell is a *Brassica* cell. In another aspect, a canola cell is a *Brassica rapa* cell. In an aspect, a tobacco cell is a *Nicotiana benthamiana* cell. In an aspect, a tobacco cell is a *Nicotiana tabacum* cell. In an aspect, an algae cell is a *Chlorella* cell or a *Volvox* cell.

In an aspect, a population of fungal cells is selected from the group consisting of a population of *Penicillium* cells, a population of *Saccharomyces* cells, a population of *Aspergillus* cells, a population of *Rhizopus* cells, a population of *Neurospora* cells, a population of *Schizosaccharomyces* cells, and a population of *Candida* cells. In an aspect, a *Saccharomyces* cell is a *Saccharomyces cerevisiae* cell. In an aspect, a *Schizosaccharomyces* cell is a *Schizosaccharomyces pombe* cell.

In an aspect, this disclosure provides a method for isolating intact mitochondria from a tissue comprising: (a) generating a mashed tissue; (b) suspending the mashed tissue in a buffer comprising: (i) sucrose; (ii) magnesium chloride ($MgCl_2$); and (iii) 2-Amino-2-(hydroxymethyl)-1, 3-propanediol hydrochloride (Tris-HCl) to generate a cell suspension; (c) centrifuging the cell suspension to generate a supernatant; (d) centrifuging the supernatant to generate a first mitochondria-rich pellet; and (e) resuspending the first mitochondria-rich pellet in the buffer to generate a first mitochondrial suspension. In an aspect, the method further comprises (f) centrifuging the first mitochondrial suspension to generate a second mitochondria-rich pellet; (g) resuspending the second mitochondria-rich pellet in the buffer to generate a second mitochondrial suspension; (h) centrifuging the second mitochondrial suspension to generate a third mitochondria-rich pellet; and (i) resuspending the third mitochondria-rich pellet in the buffer to generate a third mitochondrial suspension.

As used herein, a "tissue" refers to an ensemble of similar cells and their extracellular matrix from the same origin that together carry out a specific function. Sometimes, multiple tissues are functionally grouped together to form an organ.

As used herein, "mashed tissue" refers to any tissue that has been cut, sliced, diced, smashed, pounded, ground, pulled, stretched, sieved, strained, filtered, or otherwise manipulated in an effort to break a starting piece of tissue into two or more smaller pieces.

In an aspect, a mashed tissue is generated by cutting a tissue into two or more pieces. In another aspect, a mashed tissue is generated by slicing a tissue into two or more pieces. In another aspect, a mashed tissue is generated by dicing a tissue into two or more pieces. In another aspect, a mashed tissue is generated by smashing a tissue into two or more pieces. In another aspect, a mashed tissue is generated by pounding a tissue into two or more pieces. In another aspect, a mashed tissue is generated by grinding a tissue into two or more pieces. In another aspect, a mashed tissue is generated by pulling a tissue into two or more pieces. In another aspect, a mashed tissue is generated by breaking a tissue into two or more pieces. In another aspect, a mashed tissue is generated by stretching a tissue into two or more pieces. In another aspect, a mashed tissue is generated by sieving a tissue into two or more pieces. In another aspect, a mashed tissue is generated by straining a tissue into two or more pieces. In another aspect, a mashed tissue is generated by filtering a tissue into two or more pieces.

In an aspect, a filter or strainer used to generate a mashed tissue comprises an average pore size of less than or equal to 100 μm. In another aspect, a filter or strainer used to generate a mashed tissue comprises an average pore size of less than or equal to 90 μm. In another aspect, a filter or strainer used to generate a mashed tissue comprises an average pore size of less than or equal to 80 μm. In another aspect, a filter or strainer used to generate a mashed tissue comprises an average pore size of less than or equal to 70 μm. In another aspect, a filter or strainer used to generate a mashed tissue comprises an average pore size of less than or equal to 60 μm. In another aspect, a filter or strainer used to generate a mashed tissue comprises an average pore size of less than or equal to 50 μm. In another aspect, a filter or strainer used to generate a mashed tissue comprises an average pore size of less than or equal to 40 μm. In another aspect, a filter or strainer used to generate a mashed tissue comprises an average pore size of less than or equal to 30 μm. In another aspect, a filter or strainer used to generate a mashed tissue comprises an average pore size of less than or equal to 20 μm.

In an aspect, a filter or strainer used to generate a mashed tissue comprises an average pore size of about 100 μm. In another aspect, a filter or strainer used to generate a mashed tissue comprises an average pore size of about 90 μm. In another aspect, a filter or strainer used to generate a mashed tissue comprises an average pore size of about 80 μm. In another aspect, a filter or strainer used to generate a mashed tissue comprises an average pore size of about 70 μm. In another aspect, a filter or strainer used to generate a mashed tissue comprises an average pore size of about 60 μm. In another aspect, a filter or strainer used to generate a mashed tissue comprises an average pore size of about 50 μm. In another aspect, a filter or strainer used to generate a mashed tissue comprises an average pore size of about 40 μm. In another aspect, a filter or strainer used to generate a mashed tissue comprises an average pore size of about 30 μm. In another aspect, a filter or strainer used to generate a mashed tissue comprises an average pore size of about 20 μm.

In an aspect, a filter or a strainer used to generate a mashed tissue comprises an average pore size between about 20 μm and about 100 μm. In another aspect, a filter or a strainer used to generate a mashed tissue comprises an average pore size between about 30 μm and about 100 μm. In another aspect, a filter or a strainer used to generate a mashed tissue comprises an average pore size between about 40 μm and about 100 μm. In another aspect, a filter or a strainer used to generate a mashed tissue comprises an average pore size between about 20 μm and about 80 μm. In another aspect, a filter or a strainer used to generate a mashed tissue comprises an average pore size between about 20 μm and about 60 μm. In another aspect, a filter or a strainer used to generate a mashed tissue comprises an average pore size between about 20 μm and about 50 μm. In another aspect, a filter or a strainer used to generate a mashed tissue comprises an average pore size between about 20 μm and about 40 μm. In another aspect, a filter or a strainer used to generate a mashed tissue comprises an average pore size between about 30 μm and about 50 μm.

In an aspect, a mortar is used to generate a mashed tissue. In another aspect, a pestle is used to generate a mashed tissue. In another aspect, scissors are used to generate a mashed tissue. In another aspect, a knife is used to generate a mashed tissue. In another aspect, a scalpel is used to generate a mashed tissue. In another aspect, a razorblade is used to generate a mashed tissue. In another aspect, a wire sieve is used to generate a mashed tissue. In another aspect, mesh is used to generate a mashed tissue. In another aspect, filter paper is used to generate a mashed tissue. In another aspect, glassware is used to generate a mashed tissue. In another aspect, a Dounce homogenizer is used to generate a mashed tissue. In an aspect, a syringe is used to generate a mashed tissue. In another aspect, a needle is used to generate a mashed tissue.

In an aspect, a tissue comprises two or more cells. In another aspect, a tissue comprises 100 or more cells. In a further aspect, a tissue comprises a group of 1000 or more cells. In another aspect, a tissue comprises 10,000 or more cells. In another aspect, a tissue comprises 100,000 or more cells. In another aspect, a tissue comprises 500,000 or more cells. In another aspect, a tissue comprises 1,000,000 or more cells. In another aspect, a tissue comprises 2,500,000 or more cells. In another aspect, a tissue comprises 5,000,000 or more cells. In another aspect, a tissue comprises 10,000,000 or more cells.

In an aspect, a tissue comprises between 1 cell and 100,000,000 cells. In another aspect, a tissue comprises between 1 cell and 50,000,000 cells. In another aspect, a tissue comprises between 1 cell and 25,000,000 cells. In another aspect, a tissue comprises between 1 cell and 10,000,000 cells. In another aspect, a tissue comprises between 1 cell and 5,000,000 cells. In another aspect, a tissue comprises between 1 cell and 2,500,000 cells. In another aspect, a tissue comprises between 1 cell and 1,000,000 cells. In another aspect, a tissue comprises between 1 cell and 500,000 cells. In another aspect, a tissue comprises between 1 cell and 250,000 cells. In another aspect, a tissue comprises between 1 cell and 100,000 cells. In another aspect, a tissue comprises between 1 cell and 50,000 cells. In another aspect, a tissue comprises between 1 cell and 25,000 cells. In another aspect, a tissue comprises between 1 cell and 10,000 cells. In another aspect, a tissue comprises between 1 cell and 5,000 cells. In another aspect, a tissue comprises between 1 cell and 1,000 cells. In another aspect, a tissue comprises between 1 cell and 500 cells. In another aspect, a tissue comprises between 100 cells and 50,000,000 cells. In another aspect, a tissue comprises between 1,000 cells and 50,000,000 cells. In another aspect, a tissue comprises between 10,000 cells and 50,000,000 cells. In another aspect, a tissue comprises between 100,000 cells and 50,000,000 cells.

In an aspect, a tissue comprises at least 0.001 grams of tissue. In an aspect, a tissue comprises at least 0.0025 grams of tissue. In an aspect, a tissue comprises at least 0.005 grams of tissue. In an aspect, a tissue comprises at least 0.01 grams of tissue. In an aspect, a tissue comprises at least 0.025 grams of tissue. In an aspect, a tissue comprises at least 0.05 grams of tissue. In an aspect, a tissue comprises at least 0.1 grams of tissue. In an aspect, a tissue comprises at least 0.25 grams of tissue. In an aspect, a tissue comprises at least 0.5 grams of tissue. In an aspect, a tissue comprises at least 1.0 grams of tissue. In an aspect, a tissue comprises at least 2.5 grams of tissue. In an aspect, a tissue comprises at least 5.0 grams of tissue. In an aspect, a tissue comprises at least 10 grams of tissue. In an aspect, a tissue comprises at least 25 grams of tissue. In an aspect, a tissue comprises at least 50 grams of tissue. In an aspect, a tissue comprises at least 100 grams of tissue.

In an aspect, a tissue comprises between 0.001 grams and 100 grams of tissue. In another aspect, a tissue comprises between 0.001 grams and 50 grams of tissue. In another aspect, a tissue comprises between 0.001 grams and 25 grams of tissue. In another aspect, a tissue comprises between 0.001 grams and 10 grams of tissue. In another aspect, a tissue comprises between 0.001 grams and 5 grams of tissue. In another aspect, a tissue comprises between 0.001 grams and 2.5 grams of tissue. In another aspect, a tissue comprises between 0.001 grams and 1 gram of tissue. In another aspect, a tissue comprises between 0.001 grams and 0.75 grams of tissue. In another aspect, a tissue comprises between 0.001 grams and 0.5 grams of tissue. In another aspect, a tissue comprises between 0.001 grams and 0.25 grams of tissue. In another aspect, a tissue comprises between 0.1 grams and 1 gram of tissue. In another aspect, a tissue comprises between 0.25 grams and 1 gram of tissue. In another aspect, a tissue comprises between 0.5 grams and 1 gram of tissue. In another aspect, a tissue comprises between 0.1 grams and 0.75 grams of tissue. In another aspect, a tissue comprises between 0.1 grams and 0.5 grams of tissue. In another aspect, a tissue comprises between 0.25 grams and 0.75 grams of tissue.

In an aspect, a tissue is an isolated tissue. As used herein, an "isolated tissue" refers to a tissue that has been grown in vitro or ex vivo. In another aspect, a tissue is harvested from a living organism. In an aspect, a tissue is harvested from a freshly deceased organism. As used herein, "freshly deceased" refers to an organism that has been considered to be deceased for less than twenty-four hours. In an aspect, a tissue is harvested via needle biopsy (a "needle biopsy tissue sample.")

In an aspect, a tissue is selected from the group consisting of a mammal tissue, a fish tissue, a reptile tissue, an amphibian tissue, an avian tissue, an insect tissue, a plant tissue.

In an aspect, a mammal tissue is selected from the group of a primate tissue, a rodent tissue, a canine tissue, a feline tissue, an artiodactyl tissue, a lagomorph tissue, a marsupial tissue, and a perissodactyl tissue.

In an aspect, a primate tissue is selected from the group consisting of a human tissue, a chimpanzee tissue, an orangutan tissue, a gorilla tissue, a bonobo tissue, and a lemur tissue. In an aspect, human tissues are *Homo sapiens* tissues. In an aspect, chimpanzee tissues are *Pan troglodytes* tissues. In an aspect, orangutan tissues are *Pongo pygmaeus* tissues, *Pongo abelii* tissues, or *Pongo tapanuliensis* tissues. In an aspect, gorilla tissues are *Gorilla gorilla* tissues or *Gorilla beringei* tissues. In an aspect, bonobo tissues are Pan paniscus tissues. In an aspect, lemur tissues are superfamily Lemuroidea tissues.

In an aspect, a rodent tissue is selected from the group consisting of a mouse tissue and a rat tissue. In an aspect, a mouse tissue is a *Mus musculus* tissue. In an aspect, a mouse tissue is a *Peromyscus leucopus* tissue. In another aspect, a mouse tissue is a *Peromyscus maniculatus* tissue. In an aspect, a rat tissue is a *Rattus norvegicus* tissue. In another aspect, a rat tissue is a *Rattus norvegicus domestica* tissue.

In an aspect, an artiodactyl tissue is selected from the group consisting of a cattle tissue, a deer tissue, a sheep tissue, a pig tissue, and a goat tissue. In an aspect, a cattle tissue is a *Bos taurus* tissue. In an aspect, a deer tissue is a family Cervidae tissue. In another aspect, a deer tissue is a *Cervus* tissue. In another aspect, a deer tissue is an *Odocoileus* tissue. In another aspect, a deer tissue is an *Alces* tissue. In another aspect, a deer tissue is a *Rangifer* tissue. In an aspect, a sheep tissue is an *Ovis aries* tissue. In an aspect, a pig tissue is a *Sus scrofa* tissue. In another aspect, a pig tissue is a *Sus scrofa domesticus* tissue. In an aspect, a goat tissue is a *Capra aegagrus* tissue. In another aspect, a goat tissue is a *Capra aegagrus hircus* tissue.

In an aspect, a perissodactyl tissue is a horse tissue. In an aspect, a horse tissue is an *Equus ferus* tissue. In another aspect, a horse tissue is an *Equus ferus caballus* tissue.

In an aspect, a plant tissue is selected from the group consisting of an *Arabidopsis* tissue, a corn tissue, a rice tissue, a soybean tissue, a wheat tissue, a sorghum tissue, an alfalfa tissue, a *Triticale* tissue, a tomato tissue, a potato tissue, a cucumber tissue, a canola tissue, a tobacco tissue, an algae tissue, and a *Selaginella* tissue.

In an aspect, a plant tissue is a gymnosperm tissue. In an aspect, a plant tissue is an angiosperm tissue. In an aspect, a plant tissue is a dicotyledonous tissue. In an aspect, a plant tissue is a monocotyledonous tissue.

In an aspect, an *Arabidopsis* tissue is an *Arabidopsis thaliana* tissue. In an aspect, a corn tissue is a *Zea mays* tissue. In an aspect, a rice tissue is an *Oryza sativa* tissue or an *Oryza rufipogon* tissue. In an aspect, a soybean tissue is a *Glycine max* tissue. In an aspect, a wheat tissue is a *Triticum aestivum* tissue, a *Triticum spelta* tissue, or a *Triticum durum* tissue. In an aspect, a sorghum tissue is a *Sorghum bicolor* tissue. In an aspect, an alfalfa tissue is a *Medicago sativa* tissue. In an aspect, a tomato tissue is a *Solanum lycopersicum* tissue. In an aspect, a potato tissue is a *Solanum tuberosum* tissue. In an aspect, a cucumber tissue is a *Cucumis sativus* tissue. In an aspect, a canola tissue is a *Brassica* tissue. In another aspect, a canola tissue is a *Brassica rapa* tissue. In an aspect, a tobacco tissue is a *Nicotiana benthamiana* tissue. In an aspect, a tobacco tissue is a *Nicotiana tabacum* tissue.

In an aspect, a tissue is selected from the group consisting of nervous tissue, muscle tissue, epithelial tissue, and connective tissue. In an aspect, a muscle tissue is selected from the group consisting of a cardiac muscle tissue, a smooth muscle tissue, and a skeletal muscle tissue. In an aspect, a nervous tissue is selected from the group consisting of brain tissue, spinal cord tissue, and nerve tissue.

In an aspect, a tissue is selected from the group consisting of a brain tissue, a thyroid tissue, a thymus tissue, a heart tissue, a lung tissue, a liver tissue, a kidney tissue, a stomach tissue, a pancreas tissue, an intestinal tissue, a spinal tissue, an appendix tissue, a gallbladder tissue, an ovarian tissue, a testicular tissue, a spleen tissue, a skin tissue, a nerve tissue, and a bone tissue.

In an aspect, a plant tissue is selected from the group consisting of leaf tissue, stem tissue, floral tissue, fruit tissue, and root tissue.

As used herein, a "cell suspension" refers to on ore more free-floating cells in a liquid medium.

When a cell suspension is centrifuged, it separates into two phases: a supernatant and a precipitate. As used herein, a "supernatant" refers to the liquid phase lying above the precipitate (e.g., cells and cellular debris following the centrifugation of a cell suspension).

As used herein, a "mitochondria-rich pellet" refers to the precipitate that forms following the centrifugation of the supernatant that arises from the centrifugation of a cell suspension. In an aspect, a mitochondria-rich pellet comprises at least 2 times more mitochondria than the precipitate formed by centrifuging a cell suspension. In another aspect, a mitochondria-rich pellet comprises at least 3 times more mitochondria than the precipitate formed by centrifuging a cell suspension. In another aspect, a mitochondria-rich pellet comprises at least 4 times more mitochondria than the precipitate formed by centrifuging a cell suspension. In another aspect, a mitochondria-rich pellet comprises at least 5 times more mitochondria than the precipitate formed by centrifuging a cell suspension. In another aspect, a mitochondria-rich pellet comprises at least 6 times more mitochondria than the precipitate formed by centrifuging a cell suspension. In another aspect, a mitochondria-rich pellet comprises at least 7 times more mitochondria than the precipitate formed by centrifuging a cell suspension. In another aspect, a mitochondria-rich pellet comprises at least 8 times more mitochondria than the precipitate formed by centrifuging a cell suspension. In another aspect, a mitochondria-rich pellet comprises at least 9 times more mitochondria than the precipitate formed by centrifuging a cell suspension. In another aspect, a mitochondria-rich pellet comprises at least 10 times more mitochondria than the precipitate formed by centrifuging a cell suspension. In another aspect, a mitochondria-rich pellet comprises at least 25 times more mitochondria than the precipitate formed by centrifuging a cell suspension. In another aspect, a mitochondria-rich pellet comprises at least 50 times more mitochondria than the precipitate formed by centrifuging a cell suspension. In another aspect, a mitochondria-rich pellet comprises at least 75 times more mitochondria than the precipitate formed by centrifuging a cell suspension. In another aspect, a mitochondria-rich pellet comprises at least 100 times more mitochondria than the precipitate formed by centrifuging a cell suspension. In another aspect, a mitochondria-rich pellet comprises at least 250 times more mitochondria than the precipitate formed by centrifuging a cell suspension. In another aspect, a mitochondria-rich pellet comprises at least 500 times more mitochondria than the precipitate formed by centrifuging a cell suspension. In another aspect, a mitochondria-rich pellet comprises at least 1000 times more mitochondria than the precipitate formed by centrifuging a cell suspension. In another aspect, a mitochondria-rich pellet comprises at least 2500 times more mitochondria than the precipitate formed by centrifuging a cell suspension. In another aspect, a mitochondria-rich pellet comprises at least 5000 times more mitochondria than the precipitate formed by centrifuging a cell suspension.

As used herein, "suspending" or "resuspending" refers to dispersing a composition (e.g., cells, tissues, mitochondria) throughout a liquid (e.g., a buffer). For example, suspending a population of cells refers to dispersing the population of cells throughout a liquid (e.g., a buffer) such that a plurality of the cells are free-floating. Those in the art would recognize that there are many suitable methods for suspending populations of cells, mashed tissues, and mitochondria-rich pellets. Without being limiting, examples of methods suitable for suspending or resuspending a composition (e.g., cells, tissues, mitochondria) in a liquid (e.g., a buffer) include pipetting, agitating, tapping, shaking, stirring, vortexing, and sonicating.

As used herein, a "mitochondrial suspension" refers to a mitochondria-rich pellet that has been resuspended in a liquid medium such that a plurality of the mitochondria are free-floating in the liquid medium upon resuspension. It will be appreciated that, over time, some mitochondria may settle in the mitochondrial suspension and require gentle agitation to become free-floating again.

In an aspect, a mitochondrial suspension is substantially free of non-mitochondrial cellular components. As used herein, a mitochondrial suspension is "substantially free" of non-mitochondrial cellular components when the mitochondrial suspension comprises no more than 35% non-mitochondrial cellular components by mass.

As used herein, "non-mitochondrial cellular components" refers to nuclei (including nuclear proteins, nuclear DNA, mRNA of nuclear origin, and nucleolus), plastids (e.g., chloroplasts, amyloplasts, chromoplasts, leucoplasts), ribosomes, tRNAs, small RNAs, vesicles, rough endoplasmic reticulum, smooth endoplasmic reticulum, Golgi bodies, vacuoles, cytosol, lysosomes, centrosomes, and cellular membranes.

In an aspect, a mitochondrial suspension comprises a DNA purity of greater than or equal to 70%. In another aspect, a mitochondrial suspension comprises a DNA purity of greater than or equal to 75%. In another aspect, a mitochondrial suspension comprises a DNA purity of greater than or equal to 80%. In another aspect, a mitochondrial suspension comprises a DNA purity of greater than or equal to 85%. In another aspect, a mitochondrial suspension comprises a DNA purity of greater than or equal to 90%. In another aspect, a mitochondrial suspension comprises a DNA purity of greater than or equal to 95%. In another aspect, a mitochondrial suspension comprises a DNA purity of 100%.

In an aspect, a mitochondrial suspension comprises a DNA purity of between 50% and 100%. In another aspect, a mitochondria suspension comprises a DNA purity of between 60% and 100%. In another aspect, a mitochondria suspension comprises a DNA purity of between 70% and 100%. In another aspect, a mitochondria suspension comprises a DNA purity of between 80% and 100%. In another aspect, a mitochondria suspension comprises a DNA purity of between 90% and 100%. In another aspect, a mitochondria suspension comprises a DNA purity of between 95% and 100%.

As used herein, a "DNA purity" refers to the ratio of mitochondrial DNA (mtDNA) to nuclear DNA (nDNA) in the mitochondrial suspension as expressed by a percentage. A DNA purity of greater than or equal to 70% means that ≥70% of the DNA in the mitochondrial suspension is mtDNA and ≤30% of the DNA in the mitochondrial suspension is nDNA. Similarly, a DNA purity of greater than or equal to 85% means that that ≥85% of the DNA in the mitochondrial suspension is mtDNA and ≤15% of the DNA in the mitochondrial suspension is nDNA. A mitochondrial suspension with 100% DNA purity would comprise only mtDNA and have no detectable nDNA. Methods are known in the art for determining the ratio of mtDNA to nDNA in a given sample. See, for example, Quiros et al., "Analysis of mtDNA/nDNA ratio in mice," *Curr. Protoc. Mouse Biol.,* 7:47-54 (2017).

In an aspect, a mitochondrial suspension comprises a protein purity of great than or equal to 70%. In another aspect, a mitochondrial suspension comprises a protein purity of greater than or equal to 75%. In another aspect, a mitochondrial suspension comprises a protein purity of greater than or equal to 80%. In another aspect, a mitochondrial suspension comprises a protein purity of greater than or equal to 85%. In another aspect, a mitochondrial suspension comprises a protein purity of greater than or equal to 90%. In another aspect, a mitochondrial suspension comprises a protein purity of greater than or equal to 95%. In another aspect, a mitochondrial suspension comprises a protein purity of 100%.

In an aspect, a mitochondrial suspension comprises a protein purity of between 50% and 100%. In another aspect, a mitochondria suspension comprises a protein purity of between 60% and 100%. In another aspect, a mitochondria suspension comprises a protein purity of between 70% and 100%. In another aspect, a mitochondria suspension comprises a protein purity of between 80% and 100%. In another aspect, a mitochondria suspension comprises a protein purity of between 90% and 100%. In another aspect, a mitochondria suspension comprises a protein purity of between 95% and 100%.

As used herein, a "protein purity" refers to the ratio of mitochondrial protein to non-mitochondrial protein (e.g., without being limiting, nuclear proteins, cytosolic proteins, cell wall proteins, plasma membrane proteins) in the mitochondrial suspension as expressed by a percentage. A protein purity of greater than or equal to 70% means that ≥70% of the protein in the mitochondrial suspension is mitochondrial protein and ≤30% of the protein in the mitochondrial suspension is non-mitochondrial protein. Similarly, a protein purity of greater than or equal to 85% means that that ≥85% of the protein in the mitochondrial suspension is mitochondrial protein and ≤15% of the protein in the mitochondrial suspension is non-mitochondrial protein. A mitochondrial suspension with 100% protein purity would comprise only mitochondrial protein and have no detectable non-mitochondrial protein. Methods of determining which proteins are in a given sample are well known in the art. For example, without being limiting, methods such as Western blotting, ELISA, protein mass spectrometry (e.g., electrospray ionization (ESI); matrix-assisted laser desorption/ionization (MALDI)), two-dimensional gel electrophoresis, isoelectric focusing, chromatography, Edman degradation, and light scattering (e.g., batch dynamic light scattering; static light scattering; charge and zeta potential) can be used to determine which proteins are in a given sample.

The ratio of a single mitochondrial structural protein to a single nuclear structural protein can be used to gauge the purity of a mitochondrial suspension. In another aspect, a mitochondrial suspension comprises a ratio of a mitochondrial structural protein to nuclear structural protein of at least 1.5:1. In another aspect, a mitochondrial suspension comprises a ratio of a mitochondrial structural protein to nuclear structural protein of at least 2:1. In another aspect, a mitochondrial suspension comprises a ratio of a mitochondrial structural protein to nuclear structural protein of at least 3:1. In another aspect, a mitochondrial suspension comprises a ratio of a mitochondrial structural protein to nuclear structural protein of at least 4:1. In another aspect, a mitochondrial suspension comprises a ratio of a mitochondrial structural protein to nuclear structural protein of at least 5:1. In another aspect, a mitochondrial suspension comprises a ratio of a mitochondrial structural protein to nuclear structural protein of at least 6:1. In another aspect, a mitochondrial suspension comprises a ratio of a mitochondrial structural protein to nuclear structural protein of at least 7:1. In another aspect, a mitochondrial suspension comprises a ratio of a mitochondrial structural protein to nuclear structural protein of at least 8:1. In another aspect, a mitochondrial suspension comprises a ratio of a mitochondrial structural protein to nuclear structural protein of at least 9:1. In another aspect, a mitochondrial suspension comprises a ratio of a mitochondrial structural protein to nuclear structural protein of at least 10:1. In another aspect, a mitochondrial suspension comprises a ratio of a mitochondrial structural protein to nuclear structural protein of at least 12.5:1. In another aspect, a mitochondrial suspension comprises a ratio of a mitochondrial structural protein to nuclear structural protein of at least 15:1. In another aspect, a mitochondrial suspension comprises a ratio of a mitochondrial structural protein to nuclear structural protein of at least 17.5:1. In another aspect, a mitochondrial suspension comprises a ratio of a mitochondrial structural protein to nuclear structural protein of at least 20:1. In another aspect, a mitochondrial suspension comprises a ratio of a mitochondrial structural protein to nuclear structural protein of at least 25:1. In another aspect, a mitochondrial suspension comprises a ratio of a mitochondrial structural protein to nuclear structural protein of at least 30:1. In another aspect, a mitochondrial suspension comprises a ratio of a mitochondrial structural protein to nuclear structural protein of at least 35:1. In another aspect, a mitochondrial suspension comprises a ratio of a mitochondrial structural protein to nuclear structural protein of at least 40:1. In another aspect, a mitochondrial suspension comprises a ratio of a mitochondrial structural protein to nuclear structural protein of at least 45:1. In another aspect, a mitochondrial suspension comprises a ratio of a mitochondrial structural protein to nuclear structural protein of at least 50:1. In another aspect, a mitochondrial suspension comprises a ratio of a mitochondrial structural protein to nuclear structural protein of at least 60:1. In another aspect, a mitochondrial suspension comprises a ratio of a mitochondrial structural protein to nuclear structural protein of at least 70:1. In another aspect, a mitochondrial suspension comprises a ratio of a mitochondrial structural protein to nuclear structural protein of at least 80:1. In another aspect, a mitochondrial suspension comprises a ratio of a mitochondrial structural protein to nuclear structural protein of at least 90:1. In another aspect, a mitochondrial suspension comprises a ratio of a mitochondrial structural protein to nuclear structural protein of at least 100:1. In another aspect, a mitochondrial suspension comprises a ratio of a mitochondrial structural protein to nuclear structural protein of at least 250:1.

In an aspect, a mitochondrial suspension comprises a ratio of a mitochondrial structural protein to nuclear structural protein of between 1.5:1 and 250:1. In another aspect, a mitochondrial suspension comprises a ratio of a mitochondrial structural protein to nuclear structural protein of between 2:1 and 250:1. In another aspect, a mitochondrial suspension comprises a ratio of a mitochondrial structural protein to nuclear structural protein of between 5:1 and 250:1. In another aspect, a mitochondrial suspension comprises a ratio of a mitochondrial structural protein to nuclear structural protein of between 9:1 and 250:1. In another aspect, a mitochondrial suspension comprises a ratio of a mitochondrial structural protein to nuclear structural protein of between 10:1 and 250:1. In another aspect, a mitochondrial suspension comprises a ratio of a mitochondrial structural protein to nuclear structural protein of between 12.5:1 and 250:1. In another aspect, a mitochondrial suspension comprises a ratio of a mitochondrial structural protein to nuclear structural protein of between 15:1 and 250:1. In another aspect, a mitochondrial suspension comprises a ratio of a mitochondrial structural protein to nuclear structural protein of between 17.5:1 and 250:1. In another aspect, a mitochondrial suspension comprises a ratio of a mitochondrial structural protein to nuclear structural protein of between 20:1 and 250:1. In another aspect, a mitochondrial suspension comprises a ratio of a mitochondrial structural protein to nuclear structural protein of between 25:1 and 250:1. In another aspect, a mitochondrial suspension comprises a ratio of a mitochondrial structural protein to nuclear structural protein of between 50:1 and 250:1. In another aspect, a mitochondrial suspension comprises a ratio of a mitochondrial structural protein to nuclear structural protein of between 100:1 and 250:1. In another aspect, a mitochondrial suspension comprises a ratio of a mitochondrial structural protein to nuclear structural protein of between 1.5:1 and 100:1. In another aspect, a mitochondrial suspension comprises a ratio of a mitochondrial structural protein to nuclear structural protein of between 1.5:1 and 50:1. In another aspect, a mitochondrial suspension comprises a ratio of a mitochondrial structural protein to nuclear structural protein of between 1.5:1 and 25:1. In another aspect, a mitochondrial suspension comprises a ratio of a mitochondrial structural protein to nuclear structural protein of between 1.5:1 and 10:1. In another aspect, a mitochondrial suspension comprises a ratio of a mitochondrial structural protein to nuclear structural protein of between 9:1 and 100:1. In another aspect, a mitochondrial suspension comprises a ratio of a mitochondrial structural protein to nuclear structural protein of between 9:1 and 50:1. In another aspect, a mitochondrial suspension comprises a ratio of a mitochondrial structural protein to nuclear structural protein of between 9:1 and 25:1. In another aspect, a mitochondrial suspension comprises a ratio of a mitochondrial structural protein to nuclear structural protein of between 9:1 and 20:1. In another aspect, a mitochondrial suspension comprises a ratio of a mitochondrial structural protein to nuclear structural protein of between 9:1 and 15:1.

In an aspect, any known mitochondrial structural protein and any known nuclear structural protein can be used to determine the ratio of mitochondrial structural proteins to nuclear structural proteins in a mitochondrial suspension. Mitochondrial DNA sequences and the proteins they encode are well known in the art. See Smith, *Brief Funct. Genomics*, 15:47-54 (2016). Additionally, nuclear structural protein sequences can be obtained from many sequenced reference genomes that are publicly available. See, for example, Clark et al., "GenBank," *Nucleic Acids Res.*, 44:D67-D72 (2016); and online at ncbi[dot]nlm[dot]nih[dot]gov/genbank/.

Non-limiting examples of mitochondrial structural proteins include fatty-acyl-CoA synthase, carnitine acyl transferase, TOM complex, carnitine acetyltransferase, NADH/ubiquinone oxidoreductase, ubiquinone, cytochrome c reductase, cytochrome c oxidase, succinate dehydrogenase, and mitochondrial ATP synthase. In an aspect, a mitochondrial structural protein is selected from the group consisting of fatty-acyl-CoA synthase, carnitine acyl transferase, TOM complex, carnitine acetyltransferase, NADH/ubiquinone oxidoreductase, ubiquinone, cytochrome c reductase, cytochrome c oxidase, succinate dehydrogenase, and mitochondrial ATP synthase. In another aspect, a mitochondrial structural protein is fatty-acyl-CoA synthase. In another aspect, a mitochondrial structural protein is carnitine acyl transferase. In another aspect, a mitochondrial structural protein is a TOM complex. In another aspect, a mitochondrial structural protein is carnitine acyltransferase. In another aspect, a mitochondrial structural protein is NADH/ubiquinone oxidoreductase. In another aspect, a mitochondrial structural protein is ubiquinone. In another aspect, a mitochondrial structural protein is cytochrome c reductase. In another aspect, a mitochondrial structural protein is cytochrome c oxidase. In another aspect, a mitochondrial structural protein is succinate dehydrogenase. In another aspect, a mitochondrial structural protein is mitochondrial ATP synthase. In another aspect, a mitochondrial structural protein is a cytochrome c protein. As used herein, a "cytochrome c protein" refers to cytochrome c reductase and cytochrome c oxidase.

Non-limiting examples of nuclear structural proteins include lamin A, lamin B1, lamin B2, NuMA, lamin C, nesprin, emerin, lamina-associated proteinl (LAP1), LAP2, lamin B receptor (LBR), nurim, MAN1, Barrier to Autointegration Factor (BAF), and Heterochromatin Proteinl (HP1). In an aspect, a nuclear structural protein is selected from the group consisting of lamin A, lamin B1, lamin B2, NuMA, lamin C, nesprin, emerin, lamina-associated proteinl (LAP1), LAP2, lamin B receptor (LBR), nurim, MAN1, Barrier to Autointegration Factor (BAF), and Heterochromatin Proteinl (HP1). In another aspect, a nuclear structural protein is lamin A. In another aspect, a nuclear structural protein is lamin B1. In another aspect, a nuclear structural protein is lamin B2. In another aspect, a nuclear structural protein is NuMA. In another aspect, a nuclear structural protein is lamin B. As used herein, "lamin B" refers to lamin B1 and lamin B2. In another aspect, a nuclear structural protein is lamin C. In another aspect, a nuclear structural protein is nesprin. In another aspect, a nuclear structural protein is emerin. In another aspect, a nuclear structural protein is LAP1. In another aspect, a nuclear structural protein is LAP2. In another aspect, a nuclear structural protein is LBR. In another aspect, a nuclear structural protein is nurim. In another aspect, a nuclear structural protein is MAN1. In another aspect, a nuclear structural protein is BAF. In another aspect, a nuclear structural protein is HP1.

As used herein, a "protease inhibitor" refers to a molecule that inhibits the function of proteases. Proteases are enzymes that catalyze, or participate in, proteolysis. In an aspect, a buffer comprises at least one protease inhibitor. In another aspect, a buffer comprises at least two protease inhibitors. In another aspect, a buffer comprises at least three protease inhibitors. In another aspect, a buffer comprises at least four protease inhibitors. In another aspect, a buffer comprises at least five protease inhibitors.

In an aspect, a protease inhibitor is an aspartic protease inhibitor. In another aspect, a protease inhibitor is a cysteine protease inhibitor. In another aspect, a protease inhibitor is a metalloprotease inhibitor. In another aspect, a protease inhibitor is a serine protease inhibitor. In another aspect, a protease inhibitor is a threonine protease inhibitor. In another aspect, a protease inhibitor is a trypsin inhibitor. In an aspect, a protease inhibitor is selected from the group consisting of an aspartic protease inhibitor, a cysteine protease inhibitor, a metalloprotease inhibitor, a serine protease inhibitor, a threonine protease inhibitor, and a trypsin inhibitor.

As used herein, a "DNase inhibitor" refers to a molecule that inhibits the function of a deoxyribonuclease (DNase). A DNase is an enzyme that catalyzes, or participates in, the hydrolytic cleavage of phosphodiester linkages in a DNA backbone. In an aspect, a buffer comprises at least one DNase inhibitor. In another aspect, a buffer comprises at least two DNase inhibitors. In another aspect, a buffer comprises at least three DNase inhibitors. In another aspect, a buffer comprises at least four DNase inhibitors. In another aspect, a buffer comprises at least five DNase inhibitors.

As used herein, a "RNase inhibitor" refers to a molecule that inhibits the function of a ribonuclease (RNase). A RNase is an enzyme that catalyzes, or participates in, the hydrolytic cleavage of phosphodiester linkages in a RNA backbone. In an aspect, a buffer comprises at least one RNase inhibitor. In another aspect, a buffer comprises at least two RNase inhibitors. In another aspect, a buffer comprises at least three RNase inhibitors. In another aspect, a buffer comprises at least four RNase inhibitors. In another aspect, a buffer comprises at least five RNase inhibitors.

In an aspect, a RNase inhibitor is a murine RNase inhibitor.

In an aspect, the temperature of a buffer is less than or equal to 15° C. In another aspect, the temperature of a buffer is less than or equal to 12° C. In another aspect, the temperature of a buffer is less than or equal to 10° C. In another aspect, the temperature of a buffer is less than or equal to 9° C. In another aspect, the temperature of a buffer is less than or equal to 8° C. In another aspect, the temperature of a buffer is less than or equal to 7° C. In another aspect, the temperature of a buffer is less than or equal to 6° C. In another aspect, the temperature of a buffer is less than or equal to 5° C. In another aspect, the temperature of a buffer is less than or equal to 4° C. In another aspect, the temperature of a buffer is less than or equal to 3° C. In another aspect, the temperature of a buffer is less than or equal to 2° C. In another aspect, the temperature of a buffer is less than or equal to 1° C.

In an aspect, the temperature of a buffer is less than or equal and about 15° C. In another aspect, the temperature of a buffer is less than or equal and about 12° C. In another aspect, the temperature of a buffer is less than or equal and about 10° C. In another aspect, the temperature of a buffer is less than or equal and about 9° C. In another aspect, the temperature of a buffer is less than or equal and about 8° C. In another aspect, the temperature of a buffer is less than or equal and about 7° C. In another aspect, the temperature of a buffer is less than or equal and about 6° C. In another aspect, the temperature of a buffer is less than or equal and about 5° C. In another aspect, the temperature of a buffer is less than or equal and about 4° C. In another aspect, the temperature of a buffer is less than or equal and about 3° C. In another aspect, the temperature of a buffer is less than or equal and about 2° C. In another aspect, the temperature of a buffer is less than or equal and about 1° C.

In an aspect, the temperature of a buffer is between 0° C. and about 15° C. In another aspect, the temperature of a buffer is between 0° C. and about 12° C. In another aspect, the temperature of a buffer is between 0° C. and about 10° C. In another aspect, the temperature of a buffer is between 0° C. and about 9° C. In another aspect, the temperature of a buffer is between 0° C. and about 8° C. In another aspect, the temperature of a buffer is between 0° C. and about 7° C. In another aspect, the temperature of a buffer is between 0° C. and about 6° C. In another aspect, the temperature of a buffer is between 0° C. and about 5° C. In another aspect, the temperature of a buffer is between 0° C. and about 4° C. In another aspect, the temperature of a buffer is between 0° C. and about 3° C. In another aspect, the temperature of a buffer is between 0° C. and about 2° C. In another aspect, the temperature of a buffer is between 0° C. and about 1° C. In another aspect, the temperature of a buffer is between about 1° C. and about 10° C. In another aspect, the temperature of a buffer is between about 1° C. and about 5° C. In another aspect, the temperature of a buffer is between about 2° C. and about 8° C. In another aspect, the temperature of a buffer is between about 2° C. and about 6° C. In another aspect, the temperature of a buffer is between about 3° C. and about 5° C.

In an aspect, a buffer comprises a sucrose concentration of less than or equal to 800 mM. In another aspect, a buffer comprises a sucrose concentration of less than or equal to 700 mM. In another aspect, a buffer comprises a sucrose concentration of less than or equal to 600 mM. In another aspect, a buffer comprises a sucrose concentration of less than or equal to 500 mM. In another aspect, a buffer comprises a sucrose concentration of less than or equal to 400 mM. In another aspect, a buffer comprises a sucrose concentration of less than or equal to 300 mM. In another aspect, a buffer comprises a sucrose concentration of less than or equal to 290 mM. In another aspect, a buffer comprises a sucrose concentration of less than or equal to 280 mM. In another aspect, a buffer comprises a sucrose concentration of less than or equal to 275 mM. In another aspect, a buffer comprises a sucrose concentration of less than or equal to 270 mM. In another aspect, a buffer comprises a sucrose concentration of less than or equal to 265 mM. In another aspect, a buffer comprises a sucrose concentration of less than or equal to 260 mM. In another aspect, a buffer comprises a sucrose concentration of less than or equal to 255 mM. In another aspect, a buffer comprises a sucrose concentration of less than or equal to 250 mM. In another aspect, a buffer comprises a sucrose concentration of less than or equal to 240 mM. In another aspect, a buffer comprises a sucrose concentration of less than or equal to 230 mM. In another aspect, a buffer comprises a sucrose concentration of less than or equal to 220 mM. In another aspect, a buffer comprises a sucrose concentration of less than or equal to 210 mM. In another aspect, a buffer comprises a sucrose concentration of less than or equal to 200 mM.

In an aspect, a buffer comprises a sucrose concentration of about 700 mM. In an aspect, a buffer comprises a sucrose concentration of about 600 mM. In an aspect, a buffer comprises a sucrose concentration of about 500 mM. In an aspect, a buffer comprises a sucrose concentration of about 400 mM. In an aspect, a buffer comprises a sucrose concentration of about 300 mM. In an aspect, a buffer comprises a sucrose concentration of about 290 mM. In an aspect, a buffer comprises a sucrose concentration of about 280 mM. In an aspect, a buffer comprises a sucrose concentration of about 270 mM. In an aspect, a buffer comprises a sucrose concentration of about 260 mM. In an aspect, a buffer comprises a sucrose concentration of about 250 mM. In an aspect, a buffer comprises a sucrose concentration of about 240 mM. In an aspect, a buffer comprises a sucrose concentration of about 230 mM. In an aspect, a buffer comprises a sucrose concentration of about 220 mM. In an aspect, a buffer comprises a sucrose concentration of about 210 mM. In an aspect, a buffer comprises a sucrose concentration of about 200 mM.

In an aspect, a buffer comprises a sucrose concentration of between about 200 mM and about 700 mM. In another aspect, a buffer comprises a sucrose concentration of between about 200 mM and about 600 mM. In another aspect, a buffer comprises a sucrose concentration of between about 200 mM and about 500 mM. In another aspect, a buffer comprises a sucrose concentration of between about 200 mM and about 400 mM. In another aspect, a buffer comprises a sucrose concentration of between about 200 mM and about 300 mM. In another aspect, a buffer comprises a sucrose concentration of between about 200 mM and about 275 mM. In another aspect, a buffer comprises a sucrose concentration of between about 200 mM and about 250 mM. In another aspect, a buffer comprises a sucrose concentration of between about 100 mM and about 500 mM. In another aspect, a buffer comprises a sucrose concentration of between about 100 mM and about 300 mM. In another aspect, a buffer comprises a sucrose concentration of between about 225 mM and about 275 mM. In another aspect, a buffer comprises a sucrose concentration of between about 240 mM and about 260 mM.

In an aspect, a buffer comprises a magnesium chloride ($MgCl_2$) concentration of less than or equal to 25 mM. In another aspect, a buffer comprises a $MgCl_2$ concentration of less than or equal to 20 mM. In another aspect, a buffer comprises a $MgCl_2$ concentration of less than or equal to 15 mM. In another aspect, a buffer comprises a $MgCl_2$ concentration of less than or equal to 10 mM. In another aspect, a buffer comprises a $MgCl_2$ concentration of less than or equal to 9 mM. In another aspect, a buffer comprises a $MgCl_2$ concentration of less than or equal to 8 mM. In another aspect, a buffer comprises a $MgCl_2$ concentration of less than or equal to 7 mM. In another aspect, a buffer comprises a $MgCl_2$ concentration of less than or equal to 6 mM. In another aspect, a buffer comprises a $MgCl_2$ concentration of less than or equal to 5 mM. In another aspect, a buffer comprises a $MgCl_2$ concentration of less than or equal to 4 mM. In another aspect, a buffer comprises a $MgCl_2$ concentration of less than or equal to 3 mM.

In an aspect, a buffer comprises a $MgCl_2$ concentration of about 25 mM. In another aspect, a buffer comprises a $MgCl_2$ concentration of about 20 mM. In another aspect, a buffer comprises a $MgCl_2$ concentration of about 15 mM. In another aspect, a buffer comprises a $MgCl_2$ concentration of about 10 mM. In another aspect, a buffer comprises a $MgCl_2$ concentration of about 9 mM. In another aspect, a buffer comprises a $MgCl_2$ concentration of about 8 mM. In another aspect, a buffer comprises a $MgCl_2$ concentration of about 7 mM. In another aspect, a buffer comprises a $MgCl_2$ concentration of about 6 mM. In another aspect, a buffer comprises a $MgCl_2$ concentration of about 5 mM. In another aspect, a buffer comprises a $MgCl_2$ concentration of about 4 mM. In another aspect, a buffer comprises a $MgCl_2$ concentration of about 3 mM.

In an aspect, a buffer comprises a $MgCl_2$ concentration of between about 1 mM and about 20 mM. In another aspect, a buffer comprises a $MgCl_2$ concentration of between about 1 mM and about 15 mM. In another aspect, a buffer comprises a $MgCl_2$ concentration of between about 1 mM and about 10 mM. In another aspect, a buffer comprises a $MgCl_2$ concentration of between about 1 mM and about 7.5 mM. In another aspect, a buffer comprises a $MgCl_2$ concentration of between about 1 mM and about 6 mM. In another aspect, a buffer comprises a $MgCl_2$ concentration of between about 1 mM and about 5 mM. In another aspect, a buffer comprises a $MgCl_2$ concentration of between about 2.5 mM and about 10 mM. In another aspect, a buffer comprises a $MgCl_2$ concentration of between about 2.5 mM and about 7.5 mM. In another aspect, a buffer comprises a $MgCl_2$ concentration of between about 2.5 mM and about 5 mM. In another aspect, a buffer comprises a $MgCl_2$ concentration of between about 4 mM and about 6 mM. In another aspect, a buffer comprises a $MgCl_2$ concentration of between about 5 mM and about 15 mM. In another aspect, a buffer comprises a $MgCl_2$ concentration of between about 5 mM and about 10 mM.

In an aspect, a buffer comprises a 2-Amino-2-(hydroxymethyl)-1,3-propanediol hydrochloride (Tris-HCl) concentration of less than or equal to 25 mM. In another aspect, a buffer comprises a Tris-HCl concentration of less than or equal to 20 mM. In another aspect, a buffer comprises a Tris-HCl concentration of less than or equal to 15 mM. In another aspect, a buffer comprises a Tris-HCl concentration of less than or equal to 12.5 mM. In another aspect, a buffer comprises a Tris-HCl concentration of less than or equal to 10 mM. In another aspect, a buffer comprises a Tris-HCl concentration of less than or equal to 7.5 mM.

In an aspect, a buffer comprises a Tris-HCl concentration of about 25 mM. In another aspect, a buffer comprises a Tris-HCl concentration of about 20 mM. In another aspect, a buffer comprises a Tris-HCl concentration of about 15 mM. In another aspect, a buffer comprises a Tris-HCl concentration of about 12.5 mM. In another aspect, a buffer comprises a Tris-HCl concentration of about 10 mM. In another aspect, a buffer comprises a Tris-HCl concentration of about 7.5 mM.

In an aspect, a buffer comprises a Tris-HCl concentration of between about 5 mM and about 25 mM. In another aspect, a buffer comprises a Tris-HCl concentration of between about 5 mM and about 20 mM. In another aspect, a buffer comprises a Tris-HCl concentration of between about 5 mM and about 15 mM. In another aspect, a buffer comprises a Tris-HCl concentration of between about 5 mM and about 12.5 mM. In another aspect, a buffer comprises a Tris-HCl concentration of between about 5 mM and about 10 mM. In another aspect, a buffer comprises a Tris-HCl concentration of between about 7.5 mM and about 15 mM. In another aspect, a buffer comprises a Tris-HCl concentration of between about 7.5 mM and about 12.5 mM. In another aspect, a buffer comprises a Tris-HCl concentration of between about 7.5 mM and about 10 mM. In another aspect, a buffer comprises a Tris-HCl concentration of between about 9 mM and about 11 mM.

In an aspect, Tris-HCl comprises a pH of less than or equal to 8.0. In another aspect, Tris-HCl comprises a pH of less than or equal to 7.9. In another aspect, Tris-HCl comprises a pH of less than or equal to 7.8. In another aspect, Tris-HCl comprises a pH of less than or equal to 7.7. In another aspect, Tris-HCl comprises a pH of less than or equal to 7.6. In another aspect, Tris-HCl comprises a pH of less than or equal to 7.5. In another aspect, Tris-HCl comprises a pH of less than or equal to 7.4. In another aspect, Tris-HCl comprises a pH of less than or equal to 7.3.

In an aspect, Tris-HCl comprises a pH of about 8.0. In another aspect, Tris-HCl comprises a pH of 1 about 7.9. In another aspect, Tris-HCl comprises a pH of about 7.8. In another aspect, Tris-HCl comprises a pH of about 7.7. In another aspect, Tris-HCl comprises a pH of about 7.6. In another aspect, Tris-HCl comprises a pH of about 7.5. In another aspect, Tris-HCl comprises a pH of about 7.4. In another aspect, Tris-HCl comprises a pH of about 7.3.

In an aspect, Tris-HCl comprises a pH of between about 7.0 and about 8.0. In another aspect, Tris-HCl comprises a pH of between about 7.2 and about 8.0. In another aspect, Tris-HCl comprises a pH of between about 7.2 and about 7.8. In another aspect, Tris-HCl comprises a pH of between about 7.2 and about 7.6. In another aspect, Tris-HCl comprises a pH of between about 7.2 and about 7.4. In another aspect, Tris-HCl comprises a pH of between about 7.3 and about 7.5.

In an aspect, a buffer comprises (a) sucrose at a concentration of about 250 mM; (b) $MgCl_2$ at a concentration of about 5 mM; and (c) Tris-HCl at a concentration of about 10 mM. In another aspect, a buffer comprises (a) sucrose at a concentration of about 250 mM; (b) $MgCl_2$ at a concentration of about 5 mM; and (c) Tris-HCl at a pH of about 7.4 and at a concentration of about 10 mM. In another aspect, a buffer comprises (a) sucrose at a concentration of between about 225 mM and about 275 mM; (b) $MgCl_2$ at a concentration of between about 2.5 mM and about 7.5 mM; and (c) Tris-HCl at a concentration of between about 5 mM and about 10 mM. In another aspect, a buffer comprises (a) sucrose at a concentration of between about 225 mM and about 275 mM; (b) $MgCl_2$ at a concentration of between about 2.5 mM and about 7.5 mM; and (c) Tris-HCl at a pH between about 7.2 and about 7.8 and at a concentration of between about 5 mM and about 10 mM.

As used herein, "centrifuging" refers to separating a mixture via spinning. Centrifugation is often performed using an instrument (e.g., a table-top centrifuge, a microcentrifuge) that is capable of rotating an object (e.g., a tube) around a fixed axis, applying a force perpendicular to the axis of spin. As an example, and without being limiting, centrifuging a cell suspension in a tube can generate a pellet of cells and cellular debris at the bottom of the tube overlaid by a liquid supernatant. Compositions with different densities or weights can collect in different layers within a tube during centrifugation, allowing one to separate, and then collect, desired fractions for additional, downstream uses.

In an aspect, centrifuging comprises the use of a table-top centrifuge. In another aspect, centrifuging comprises the use of a microcentrifuge. In another aspect, centrifuging comprises the use of a refrigerated table-top centrifuge. In another aspect, centrifuging comprises the use of a refrigerated microcentrifuge. In another aspect, centrifuging comprises the use of a centrifuge in a refrigerated room.

In an aspect, centrifuging occurs at a temperature of less than or equal to 20° C. In another aspect, centrifuging occurs at a temperature of less than or equal to 15° C. In another aspect, centrifuging occurs at a temperature of less than or equal to 12.5° C. In another aspect, centrifuging occurs at a temperature of less than or equal to 10° C. In another aspect, centrifuging occurs at a temperature of less than or equal to 7.5° C. In another aspect, centrifuging occurs at a temperature of less than or equal to 7° C. In another aspect, centrifuging occurs at a temperature of less than or equal to 6° C. In another aspect, centrifuging occurs at a temperature of less than or equal to 5° C. In another aspect, centrifuging occurs at a temperature of less than or equal to 4° C. In another aspect, centrifuging occurs at a temperature of less than or equal to 3° C. In another aspect, centrifuging occurs at a temperature of less than or equal to 2° C. In another aspect, centrifuging occurs at a temperature of less than or equal to 1° C.

In an aspect, centrifuging occurs at a temperature of about 20° C. In another aspect, centrifuging occurs at a temperature of about 15° C. In another aspect, centrifuging occurs at a temperature of about 12.5° C. In another aspect, centrifuging occurs at a temperature of about 10° C. In another aspect, centrifuging occurs at a temperature of about 7.5° C. In another aspect, centrifuging occurs at a temperature of about 7° C. In another aspect, centrifuging occurs at a temperature of about 6° C. In another aspect, centrifuging occurs at a temperature of about 5° C. In another aspect, centrifuging occurs at a temperature of about 4° C. In another aspect, centrifuging occurs at a temperature of about 3° C. In another aspect, centrifuging occurs at a temperature of about 2° C. In another aspect, centrifuging occurs at a temperature of about 1° C.

In an aspect, centrifuging occurs at a temperature between 0° C. and 20° C. In another aspect, centrifuging occurs at a temperature between 0° C. and 15° C. In another aspect, centrifuging occurs at a temperature between 0° C. and 10° C. In another aspect, centrifuging occurs at a temperature between 0° C. and 7.5° C. In another aspect, centrifuging occurs at a temperature between 0° C. and 5° C. In another aspect, centrifuging occurs at a temperature between 2° C. and 15° C. In another aspect, centrifuging occurs at a temperature between 2° C. and 7.5° C. In another aspect, centrifuging occurs at a temperature between 2° C. and 5° C.

The amount of accelerative force applied to a sample during centrifugation, the relative centrifugal force (RCF), can be measured in multiples of the standard acceleration due to gravity at the earth's surface (xg). The RCF of a specific centrifuge can be calculated using the following formula: $RCF=(RPM/1000)^2 \times r \times 11.18$, where RPM is the rotational speed of the centrifuge in revolutions per minute and r is the centrifugal radius in centimeters (distance from the center of the turning axis to the bottom of the centrifuge).

In an aspect, centrifuging of a cell suspension occurs at a relative centrifugal force of less than or equal to 1000×g. In another aspect, centrifuging of a cell suspension occurs at a relative centrifugal force of less than or equal to 900×g. In another aspect, centrifuging of a cell suspension occurs at a relative centrifugal force of less than or equal to 800×g. In another aspect, centrifuging of a cell suspension occurs at a relative centrifugal force of less than or equal to 700×g. In another aspect, centrifuging of a cell suspension occurs at a relative centrifugal force of less than or equal to 600×g. In another aspect, centrifuging of a cell suspension occurs at a relative centrifugal force of less than or equal to 500×g. In another aspect, centrifuging of a cell suspension occurs at a relative centrifugal force of less than or equal to 400×g. In another aspect, centrifuging of a cell suspension occurs at a relative centrifugal force of less than or equal to 300×g. In another aspect, centrifuging of a cell suspension occurs at a relative centrifugal force of less than or equal to 200×g. In another aspect, centrifuging of a cell suspension occurs at a relative centrifugal force of less than or equal to 100×g.

In an aspect, centrifuging of a cell suspension occurs at a relative centrifugal force of about 1000×g. In another aspect, centrifuging of a cell suspension occurs at a relative centrifugal force of about 900×g. In another aspect, centrifuging of a cell suspension occurs at a relative centrifugal force of about 800×g. In another aspect, centrifuging of a cell suspension occurs at a relative centrifugal force of about 700×g. In another aspect, centrifuging of a cell suspension occurs at a relative centrifugal force of about 600×g. In another aspect, centrifuging of a cell suspension occurs at a relative centrifugal force of about 500×g. In another aspect, centrifuging of a cell suspension occurs at a relative centrifugal force of about 400×g. In another aspect, centrifuging of a cell suspension occurs at a relative centrifugal force of about 300×g. In another aspect, centrifuging of a cell suspension occurs at a relative centrifugal force of about 200×g. In another aspect, centrifuging of a cell suspension occurs at a relative centrifugal force of about 100×g.

In an aspect, centrifuging of a cell suspension occurs at a relative centrifugal force of between about 100×g and about 1000×g. In an aspect, centrifuging of a cell suspension occurs at a relative centrifugal force of between about 200×g and about 1000×g. In an aspect, centrifuging of a cell suspension occurs at a relative centrifugal force of between about 300×g and about 1000×g. In an aspect, centrifuging of a cell suspension occurs at a relative centrifugal force of between about 400×g and about 1000×g. In an aspect, centrifuging of a cell suspension occurs at a relative centrifugal force of between about 500×g and about 1000×g. In an aspect, centrifuging of a cell suspension occurs at a relative centrifugal force of between about 600×g and about 1000×g. In an aspect, centrifuging of a cell suspension occurs at a relative centrifugal force of between about 100×g and about 700×g. In an aspect, centrifuging of a cell suspension occurs at a relative centrifugal force of between about 100×g and about 600×g. In an aspect, centrifuging of a cell suspension occurs at a relative centrifugal force of between about 200×g and about 700×g. In an aspect, centrifuging of a cell suspension occurs at a relative centrifugal force of between about 200×g and about 600×g. In an aspect, centrifuging of a cell suspension occurs at a relative centrifugal force of between about 300×g and about 700×g. In an aspect, centrifuging of a cell suspension occurs at a relative centrifugal force of between about 500×g and about 700×g.

In an aspect, a cell suspension is centrifuged for less than or equal to 30 minutes. In another aspect, a cell suspension is centrifuged for less than or equal to 25 minutes. In another aspect, a cell suspension is centrifuged for less than or equal to 20 minutes. In another aspect, a cell suspension is centrifuged for less than or equal to 17.5 minutes. In another aspect, a cell suspension is centrifuged for less than or equal to 15 minutes. In another aspect, a cell suspension is centrifuged for less than or equal to 12.5 minutes. In another aspect, a cell suspension is centrifuged for less than or equal to 10 minutes. In another aspect, a cell suspension is centrifuged for less than or equal to 7.5 minutes. In another aspect, a cell suspension is centrifuged for less than or equal to 5 minutes.

In an aspect, a cell suspension is centrifuged for about 30 minutes. In another aspect, a cell suspension is centrifuged for about 25 minutes. In another aspect, a cell suspension is centrifuged for about 20 minutes. In another aspect, a cell suspension is centrifuged for about 17.5 minutes. In another aspect, a cell suspension is centrifuged for about 15 minutes. In another aspect, a cell suspension is centrifuged for about 12.5 minutes. In another aspect, a cell suspension is centrifuged for about 10 minutes. In another aspect, a cell suspension is centrifuged for about 7.5 minutes. In another aspect, a cell suspension is centrifuged for about 5 minutes.

In an aspect, a cell suspension is centrifuged for between about 5 minutes and about 30 minutes. In another aspect, a cell suspension is centrifuged for between about 5 minutes and about 25 minutes. In another aspect, a cell suspension is centrifuged for between about 5 minutes and about 20 minutes. In another aspect, a cell suspension is centrifuged for between about 5 minutes and about 15 minutes. In another aspect, a cell suspension is centrifuged for between about 5 minutes and about 12.5 minutes. In another aspect, a cell suspension is centrifuged for between about 5 minutes and about 10 minutes. In another aspect, a cell suspension is centrifuged for between about 7.5 minutes and about 12.5 minutes. In another aspect, a cell suspension is centrifuged for between about 7.5 minutes and about 10 minutes. In another aspect, a cell suspension is centrifuged for between about 9 minutes and about 11 minutes.

In an aspect, centrifuging of a supernatant occurs at a relative centrifugal force of less than or equal to 15,000×g. In another aspect, centrifuging of a supernatant occurs at a relative centrifugal force of less than or equal to 12,500×g. In another aspect, centrifuging of a supernatant occurs at a relative centrifugal force of less than or equal to 10,000×g. In another aspect, centrifuging of a supernatant occurs at a relative centrifugal force of less than or equal to 9,900×g. In another aspect, centrifuging of a supernatant occurs at a relative centrifugal force of less than or equal to 9,800×g. In another aspect, centrifuging of a supernatant occurs at a relative centrifugal force of less than or equal to 9,750×g. In another aspect, centrifuging of a supernatant occurs at a relative centrifugal force of less than or equal to 9,500×g. In another aspect, centrifuging of a supernatant occurs at a relative centrifugal force of less than or equal to 9,000×g. In another aspect, centrifuging of a supernatant occurs at a relative centrifugal force of less than or equal to 7,500×g. In another aspect, centrifuging of a supernatant occurs at a relative centrifugal force of less than or equal to 5,000×g.

In an aspect, centrifuging of a supernatant occurs at a relative centrifugal force of about 15,000×g. In another aspect, centrifuging of a supernatant occurs at a relative centrifugal force of about 12,500×g. In another aspect, centrifuging of a supernatant occurs at a relative centrifugal force of about 10,000×g. In another aspect, centrifuging of a supernatant occurs at a relative centrifugal force of about 9,900×g. In another aspect, centrifuging of a supernatant occurs at a relative centrifugal force of about 9,800×g. In another aspect, centrifuging of a supernatant occurs at a relative centrifugal force of about 9,750×g. In another aspect, centrifuging of a supernatant occurs at a relative centrifugal force of about 9,500×g. In another aspect, centrifuging of a supernatant occurs at a relative centrifugal force of about 9,000×g. In another aspect, centrifuging of a supernatant occurs at a relative centrifugal force of about 7,500×g. In another aspect, centrifuging of a supernatant occurs at a relative centrifugal force of about 5,000×g.

In an aspect, centrifuging of a supernatant occurs at a relative centrifugal force of between about 5,000×g and about 15,000×g. In an aspect, centrifuging of a supernatant occurs at a relative centrifugal force of between about 7,500×g and about 15,000×g. In an aspect, centrifuging of a supernatant occurs at a relative centrifugal force of between about 8,000×g and about 15,000×g. In an aspect, centrifuging of a supernatant occurs at a relative centrifugal force of between about 9,000×g and about 15,000×g. In an aspect, centrifuging of a supernatant occurs at a relative centrifugal force of between about 9,500×g and about 15,000×g. In an aspect, centrifuging of a supernatant occurs at a relative centrifugal force of between about 9,750×g and about 15,000×g. In an aspect, centrifuging of a supernatant occurs at a relative centrifugal force of between about 7,500×g and about 12,500×g. In an aspect, centrifuging of a supernatant occurs at a relative centrifugal force of between about 7,500×g and about 10,000×g. In another aspect, centrifuging of a supernatant occurs at a relative centrifugal force of between about 7,500×g and about 9,800×g. In another aspect, centrifuging of a supernatant occurs at a relative centrifugal force of between about 9,000×g and about 10,000×g. In another aspect, centrifuging of a supernatant occurs at a relative centrifugal force of between about 9,250×g and about 9,800×g. In another aspect, centrifuging of a supernatant occurs at a relative centrifugal force of between about 9,500×g and about 9,800×g.

In an aspect, a supernatant is centrifuged for less than or equal to 45 minutes. In another aspect, a supernatant is centrifuged for less than or equal to 30 minutes. In another aspect, a supernatant is centrifuged for less than or equal to 25 minutes. In another aspect, a supernatant is centrifuged for less than or equal to 20 minutes. In another aspect, a supernatant is centrifuged for less than or equal to 17.5 minutes. In another aspect, a supernatant is centrifuged for less than or equal to 15 minutes. In another aspect, a supernatant is centrifuged for less than or equal to 12.5 minutes. In another aspect, a supernatant is centrifuged for less than or equal to 10 minutes. In another aspect, a supernatant is centrifuged for less than or equal to 5 minutes.

In an aspect, a supernatant is centrifuged for about 45 minutes. In another aspect, a supernatant is centrifuged for about 30 minutes. In another aspect, a supernatant is centrifuged for about 25 minutes. In another aspect, a supernatant is centrifuged for about 20 minutes. In another aspect, a supernatant is centrifuged for about 17.5 minutes. In another aspect, a supernatant is centrifuged for about 15 minutes. In another aspect, a supernatant is centrifuged for about 12.5 minutes. In another aspect, a supernatant is centrifuged for about 10 minutes. In another aspect, a supernatant is centrifuged for about 5 minutes.

In an aspect, a supernatant is centrifuged for between about 5 minutes and about 45 minutes. In another aspect, a supernatant is centrifuged for between about 10 minutes and about 45 minutes. In another aspect, a supernatant is centrifuged for between about 12.5 minutes and about 45 minutes. In another aspect, a supernatant is centrifuged for between about 15 minutes and about 45 minutes. In another aspect, a supernatant is centrifuged for between about 5 minutes and about 30 minutes. In another aspect, a supernatant is centrifuged for between about 5 minutes and about 25 minutes. In another aspect, a supernatant is centrifuged for between about 5 minutes and about 22.5 minutes. In another aspect, a supernatant is centrifuged for between about 5 minutes and about 20 minutes. In another aspect, a supernatant is centrifuged for between about 5 minutes and about 17.5 minutes. In another aspect, a supernatant is centrifuged for between about 5 minutes and about 15 minutes. In another aspect, a supernatant is centrifuged for between about 7.5 minutes and about 17.5 minutes. In another aspect, a supernatant is centrifuged for between about 7.5 minutes and about 15 minutes. In another aspect, a supernatant is centrifuged for between about 10 minutes and about 30 minutes. In another aspect, a supernatant is centrifuged for between about 10 minutes and about 20 minutes. In another aspect, a supernatant is centrifuged for between about 10 minutes and about 17.5 minutes. In another aspect, a supernatant is centrifuged for between about 10 minutes and about 15 minutes. In another aspect, a supernatant is centrifuged for between about 12.5 minutes and about 17.5 minutes. In another aspect, a supernatant is centrifuged for between about 12.5 minutes and about 15 minutes. In another aspect, a supernatant is centrifuged for between about 15 minutes and about 17.5 minutes.

In an aspect, centrifuging of a mitochondrial suspension occurs at a relative centrifugal force of less than or equal to 15,000×g. In another aspect, centrifuging of a mitochondrial suspension occurs at a relative centrifugal force of less than or equal to 12,500×g. In another aspect, centrifuging of a mitochondrial suspension occurs at a relative centrifugal force of less than or equal to 10,000×g. In another aspect, centrifuging of a mitochondrial suspension occurs at a relative centrifugal force of less than or equal to 9,900×g. In another aspect, centrifuging of a mitochondrial suspension occurs at a relative centrifugal force of less than or equal to 9,800×g. In another aspect, centrifuging of a mitochondrial suspension occurs at a relative centrifugal force of less than or equal to 9,750×g. In another aspect, centrifuging of a mitochondrial suspension occurs at a relative centrifugal force of less than or equal to 9,500×g. In another aspect, centrifuging of a mitochondrial suspension occurs at a relative centrifugal force of less than or equal to 9,000×g. In another aspect, centrifuging of a mitochondrial suspension occurs at a relative centrifugal force of less than or equal to 7,500×g. In another aspect, centrifuging of a mitochondrial suspension occurs at a relative centrifugal force of less than or equal to 5,000×g.

In an aspect, centrifuging of a mitochondrial suspension occurs at a relative centrifugal force of about 15,000×g. In another aspect, centrifuging of a mitochondrial suspension occurs at a relative centrifugal force of about 12,500×g. In another aspect, centrifuging of a mitochondrial suspension occurs at a relative centrifugal force of about 10,000×g. In another aspect, centrifuging of a mitochondrial suspension occurs at a relative centrifugal force of about 9,900×g. In another aspect, centrifuging of a mitochondrial suspension occurs at a relative centrifugal force of about 9,800×g. In another aspect, centrifuging of a mitochondrial suspension occurs at a relative centrifugal force of about 9,750×g. In another aspect, centrifuging of a mitochondrial suspension occurs at a relative centrifugal force of about 9,500×g. In another aspect, centrifuging of a mitochondrial suspension occurs at a relative centrifugal force of about 9,000×g. In another aspect, centrifuging of a mitochondrial suspension occurs at a relative centrifugal force of about 7,500×g. In another aspect, centrifuging of a mitochondrial suspension occurs at a relative centrifugal force of about 5,000×g.

In an aspect, centrifuging of a mitochondrial suspension occurs at a relative centrifugal force of between about 5,000×g and about 15,000×g. In an aspect, centrifuging of a mitochondrial suspension occurs at a relative centrifugal force of between about 7,500×g and about 15,000×g. In an aspect, centrifuging of a mitochondrial suspension occurs at a relative centrifugal force of between about 8,000×g and about 15,000×g. In an aspect, centrifuging of a mitochondrial suspension occurs at a relative centrifugal force of between about 9,000×g and about 15,000×g. In an aspect, centrifuging of a mitochondrial suspension occurs at a relative centrifugal force of between about 9,500×g and about 15,000×g. In an aspect, centrifuging of a mitochondrial suspension occurs at a relative centrifugal force of between about 9,750×g and about 15,000×g. In an aspect, centrifuging of a mitochondrial suspension occurs at a relative centrifugal force of between about 7,500×g and about 12,500×g. In an aspect, centrifuging of a mitochondrial suspension occurs at a relative centrifugal force of between about 7,500×g and about 10,000×g. In another aspect, centrifuging of a mitochondrial suspension occurs at a relative centrifugal force of between about 7,500×g and about 9,800×g. In another aspect, centrifuging of a mitochondrial suspension occurs at a relative centrifugal force of between about 9,000×g and about 10,000×g. In another aspect, centrifuging of a mitochondrial suspension occurs at a relative centrifugal force of between about 9,250×g and about 9,800×g. In another aspect, centrifuging of a mitochondrial suspension occurs at a relative centrifugal force of between about 9,500×g and about 9,800×g.

In an aspect, a mitochondrial suspension is centrifuged for less than or equal to 30 minutes. In another aspect, a mitochondrial suspension is centrifuged for less than or equal to 20 minutes. In another aspect, a mitochondrial suspension is centrifuged for less than or equal to 15 minutes. In another aspect, a mitochondrial suspension is centrifuged for less than or equal to 10 minutes. In another aspect, a mitochondrial suspension is centrifuged for less than or equal to 9 minutes. In another aspect, a mitochondrial suspension is centrifuged for less than or equal to 8 minutes. In another aspect, a mitochondrial suspension is centrifuged for less than or equal to 7 minutes. In another aspect, a mitochondrial suspension is centrifuged for less than or equal to 6 minutes. In another aspect, a mitochondrial suspension is centrifuged for less than or equal to 5 minutes. In another aspect, a mitochondrial suspension is centrifuged for less than or equal to 4 minutes. In another aspect, a mitochondrial suspension is centrifuged for less than or equal to 3 minutes. In another aspect, a mitochondrial suspension is centrifuged for less than or equal to 2 minutes. In another aspect, a mitochondrial suspension is centrifuged for less than or equal to 1 minute.

In an aspect, a mitochondrial suspension is centrifuged for about 30 minutes. In another aspect, a mitochondrial suspension is centrifuged for about 20 minutes. In another aspect, a mitochondrial suspension is centrifuged for about 15 minutes. In another aspect, a mitochondrial suspension is centrifuged for about 10 minutes. In another aspect, a mitochondrial suspension is centrifuged for about 9 minutes. In another aspect, a mitochondrial suspension is centrifuged for about 8 minutes. In another aspect, a mitochondrial suspension is centrifuged for about 7 minutes. In another aspect, a mitochondrial suspension is centrifuged for about 6 minutes. In another aspect, a mitochondrial suspension is centrifuged for about 5 minutes. In another aspect, a mitochondrial suspension is centrifuged for about 4 minutes. In another aspect, a mitochondrial suspension is centrifuged for about 3 minutes. In another aspect, a mitochondrial suspension is centrifuged for about 2 minutes. In another aspect, a mitochondrial suspension is centrifuged for about 1 minute.

In an aspect, a mitochondrial suspension is centrifuged for between about 1 minute and about 30 minutes. In another aspect, a mitochondrial suspension is centrifuged for between about 3 minutes and about 20 minutes. In another aspect, a mitochondrial suspension is centrifuged for between about 3 minutes and about 15 minutes. In another aspect, a mitochondrial suspension is centrifuged for between about 3 minutes and about 10 minutes. In another aspect, a mitochondrial suspension is centrifuged for between about 3 minutes and about 8 minutes. In another aspect, a mitochondrial suspension is centrifuged for between about 3 minutes and about 6 minutes. In another aspect, a mitochondrial suspension is centrifuged for between about 5 minutes and about 7 minutes. In another aspect, a mitochondrial suspension is centrifuged for between about 4 minutes and about 8 minutes. In another aspect, a mitochondrial suspension is centrifuged for between about 5 minutes and about 10 minutes.

In an aspect, a cell suspension comprises a volume of at least 10 µL. In another aspect, a cell suspension comprises a volume of at least 50 µL. In another aspect, a cell suspension comprises a volume of at least 100 µL. In another aspect, a cell suspension comprises a volume of at least 250 µL. In another aspect, a cell suspension comprises a volume of at least 500 µL. In another aspect, a cell suspension comprises a volume of at least 750 µL. In another aspect, a cell suspension comprises a volume of at least 1000 µL. In another aspect, a cell suspension comprises a volume of at least 1250 µL. In another aspect, a cell suspension comprises a volume of at least 1500 µL. In another aspect, a cell suspension comprises a volume of at least 1750 µL. In another aspect, a cell suspension comprises a volume of at least 2000 µL. In another aspect, a cell suspension comprises a volume of at least 5 mL. In another aspect, a cell suspension comprises a volume of at least 10 mL. In another aspect, a cell suspension comprises a volume of at least 25 mL. In another aspect, a cell suspension comprises a volume of at least 50 mL.

In an aspect, a cell suspension comprises a volume of between about 10 μL and about 50 mL. In another aspect, a cell suspension comprises a volume of between about 10 μL and about 10 mL. In another aspect, a cell suspension comprises a volume of between about 10 μL and about 2000 μL. In another aspect, a cell suspension comprises a volume of between about 10 and about 1750 μL. In another aspect, a cell suspension comprises a volume of between about 10 μL and about 1500 μL. In another aspect, a cell suspension comprises a volume of between about 10 μL and about 1000 μL. In another aspect, a cell suspension comprises a volume of between about 10 μL and about 500 μL. In another aspect, a cell suspension comprises a volume of between about 10 μL and about 250 μL. In another aspect, a cell suspension comprises a volume of between about 10 μL and about 100 μL. In another aspect, a cell suspension comprises a volume of between about 100 μL and about 2000 μL. In another aspect, a cell suspension comprises a volume of between about 100 μL and about 1000 μL. In another aspect, a cell suspension comprises a volume of between about 500 μL and about 2000 μL. In another aspect, a cell suspension comprises a volume of between about 500 μL and about 1500 μL. In another aspect, a cell suspension comprises a volume of between about 500 μL and about 1000 μL. In another aspect, a cell suspension comprises a volume of between about 1000 μL and about 2000 μL. In another aspect, a cell suspension comprises a volume of between about 5 mL and about 50 mL. In another aspect, a cell suspension comprises a volume of between about 10 mL and about 50 mL. In another aspect, a cell suspension comprises a volume of between about 25 mL and about 50 mL.

In an aspect, a mitochondrial suspension comprises a volume of between about 10 and about 10 mL. In another aspect, a mitochondrial suspension comprises a volume of between about 10 μL and about 2000 μL. In another aspect, a mitochondrial suspension comprises a volume of between about 10 μL and about 1750 μL. In another aspect, a mitochondrial suspension comprises a volume of between about 10 μL and about 1500 μL. In another aspect, a mitochondrial suspension comprises a volume of between about 10 μL and about 1000 μL. In another aspect, a mitochondrial suspension comprises a volume of between about 10 μL and about 500 μL. In another aspect, a mitochondrial suspension comprises a volume of between about 10 μL and about 250 μL. In another aspect, a mitochondrial suspension comprises a volume of between about 10 μL and about 100 μL. In another aspect, a mitochondrial suspension comprises a volume of between about 100 μL and about 2000 μL. In another aspect, a mitochondrial suspension comprises a volume of between about 100 μL and about 1000 μL. In another aspect, a mitochondrial suspension comprises a volume of between about 500 μL and about 2000 μL. In another aspect, a mitochondrial suspension comprises a volume of between about 500 μL and about 1500 μL. In another aspect, a mitochondrial suspension comprises a volume of between about 500 μL and about 1000 μL. In another aspect, a mitochondrial suspension comprises a volume of between about 1000 μL and about 2000 μL.

In an aspect, a mitochondrial suspension is stored at a temperature of less than or equal to 0° C. In another aspect, a mitochondrial suspension is stored at a temperature of less than or equal to −10° C. In another aspect, a mitochondrial suspension is stored at a temperature of less than or equal to −20° C. In another aspect, a mitochondrial suspension is stored at a temperature of less than or equal to −30° C. In another aspect, a mitochondrial suspension is stored at a temperature of less than or equal to −40° C. In another aspect, a mitochondrial suspension is stored at a temperature of less than or equal to −50° C. In another aspect, a mitochondrial suspension is stored at a temperature of less than or equal to −60° C. In another aspect, a mitochondrial suspension is stored at a temperature of less than or equal to −70° C. In another aspect, a mitochondrial suspension is stored at a temperature of less than or equal to −80° C.

In an aspect, a mitochondrial suspension is stored at a temperate of between about −80° C. and 0° C. In another aspect, a mitochondrial suspension is stored at a temperate of between about −75° C. and 0° C. In another aspect, a mitochondrial suspension is stored at a temperate of between about −70° C. and 0° C. In another aspect, a mitochondrial suspension is stored at a temperate of between about −60° C. and 0° C. In another aspect, a mitochondrial suspension is stored at a temperate of between about −50° C. and 0° C. In another aspect, a mitochondrial suspension is stored at a temperate of between about −40° C. and 0° C. In another aspect, a mitochondrial suspension is stored at a temperate of between about −30° C. and 0° C. In another aspect, a mitochondrial suspension is stored at a temperate of between about −20° C. and 0° C. In another aspect, a mitochondrial suspension is stored at a temperate of between about −10° C. and 0° C. In another aspect, a mitochondrial suspension is stored at a temperate of between about −80° C. and about −20° C. In another aspect, a mitochondrial suspension is stored at a temperate of between about −80° C. and about −60° C.

In an aspect, a method provided herein is completed in 60 minutes or less. In another aspect, a method provided herein is completed in 55 minutes or less. In another aspect, a method provided herein is completed in 45 minutes or less. In another aspect, a method provided herein is completed in 40 minutes or less. In another aspect, a method provided herein is completed in 35 minutes or less. In another aspect, a method provided herein is completed in 30 minutes or less. In another aspect, a method provided herein is completed in between 25 minutes and 50 minutes. In another aspect, a method provided herein is completed in between 25 minutes and 45 minutes. In another aspect, a method provided herein is completed in between 25 minutes and 40 minutes. In another aspect, a method provided herein is completed in between 25 minutes and 35 minutes. In another aspect, a method provided herein is completed in between 25 minutes and 30 minutes. In another aspect, a method provided herein is completed in between 30 minutes and 50 minutes. In another aspect, a method provided herein is completed in between 30 minutes and 45 minutes. In another aspect, a method provided herein is completed in between 30 minutes and 40 minutes. In another aspect, a method provided herein is completed in between 35 minutes and 50 minutes. In another aspect, a method provided herein is completed in between 35 minutes and 45 minutes. In another aspect, a method provided herein is completed in between 35 minutes and 40 minutes. As used herein, a "completed" method refers to generating a first mitochondrial suspension by following any method provided herein.

In an aspect, this disclosure provides a kit for isolating intact mitochondria from a population of cells or a tissue comprising a buffer, wherein said buffer comprises about 250 mM sucrose, about 5 mM magnesium chloride, and about 10 mM 2-Amino-2-(hydroxymethyl)-1,3-propanediol hydrochloride (Tris-HCl) (pH.7.4). In an aspect, this disclosure provides a kit for isolating intact mitochondria from a population of cells or a tissue comprising a buffer, wherein said buffer comprises about 250 mM sucrose and about 10 mM 2-Amino-2-(hydroxymethyl)-1,3-propanediol hydrochloride Tris-HCl) (pH.7.4). In an aspect, this disclosure provides a kit for isolating intact mitochondria from a population of cells or a tissue comprising a buffer, wherein said buffer comprises about 250 mM sucrose and about 5 mM magnesium chloride. In an aspect, this disclosure provides a kit for isolating intact mitochondria from a population of cells or a tissue comprising a buffer, wherein said buffer comprises about 5 mM magnesium chloride and about 10 mM 2-Amino-2-(hydroxymethyl)-1,3-propanediol hydrochloride (Tris-HCl) (pH.7.4). In an aspect, a kit further comprises at least one protease inhibitor. In another aspect, a kit further comprises at least one DNase inhibitor. In another aspect, a kit further comprises at least one RNase inhibitor. In an aspect, a protease inhibitor is a lyophilized protease inhibitor. In another aspect, a DNase inhibitor is a lyophilized DNase inhibitor. In another aspect, a RNase inhibitor is a lyophilized RNase inhibitor.

Having now generally described the disclosure, the same will be more readily understood through reference to the following examples that are provided by way of illustration, and are not intended to be limiting of the present disclosure, unless specified.

EXAMPLES

Example 1

Isolation of Intact Mitochondria from Animal Tissue

Step 1. Each sample of animal tissue is minced, and approximately 0.5 grams of tissue is mashed through a three-dimensional Falcon cell strainer with a 40 µm pore size (Fisher Scientific, Suwannee, Georgia) with the plunger from a 3 mL Kendall Monoject syringe (Tyco Healthcare Group LP, Mansfield, Massachusetts) into a plastic Petri dish (Fisher Scientific cat. no. 08-771-1) on ice. Immediately after the mashed tissue reaches the Petri dish it is mixed with 4 mL of ice-cold (e.g., between about 0° C. and about 4° C.) Buffer A (250 mM sucrose; 5 mM magnesium chloride; 10 mM Tris-HCl (pH 7.4) to create a cell suspension.

Step 2. The cell suspension is centrifuged in a tabletop microcentrifuge in 1.5 mL conical microtubes (approximately 1 mL of cell suspension per microtube) at 600×g for 10 minutes at 4° C.

Step 3. The resulting supernatant from Step 2 is removed to new 1.5 mL conical microtubes and centrifuged in a tabletop microcentrifuge at 9750×g for 15 minutes at 4° C.

Step 4. The supernatant resulting from Step 3 is removed from the conical microtubes.

Step 5. The pellet resulting from Step 3 is gently resuspended in 1.4 mL of ice-cold Buffer A.

Step 6. The resuspended pellet from Step 5 is centrifuged in a tabletop microcentrifuge at 9750×g for 6 minutes at 4° C.

Step 7. The supernatant resulting from Step 6 is transferred from the conical microtubes to new conical microtubes.

Step 8. The pellet resulting from Step 7 is gently resuspended in ice-cold Buffer A, or in another buffer of choice, and centrifuged in a tabletop microcentrifuge at 9750×g for 6 minutes at 4° C.

Step 9. The pellet resulting from step 8 is frozen to −70° C., or is resuspended in another buffer of choice, for further analysis.

Example 2

Isolation of Intact Mitochondria from Adherent Cells

Step 1. Adherent cells are rinsed in a Petri dish with ice-cold (e.g., between about 0° C. and about 4° C.) 1× phosphate-buffered saline. Cells are collected with a spatula and suspended in 4 mL of ice-cold (e.g., between about 0° C. and about 4° C.) Buffer A (see Example 1) per 1×10$^7$ cells. The suspension is passed through a 27-gauge blunt-end needle attached to a 5 mL syringe five times to produce a cell suspension.

Step 2. The cell suspension is centrifuged in a tabletop microcentrifuge in 1.5 mL conical microtubes (approximately 1 mL of cell suspension per microtube) at 600×g for 10 minutes at 4° C.

Step 3. The resulting supernatant from Step 2 is removed to new 1.5 mL conical microtubes and centrifuged in a tabletop microcentrifuge at 9750×g for 15 minutes at 4° C.

Step 4. The supernatant resulting from Step 3 is removed from the conical microtubes.

Step 5. The pellet resulting from Step 3 is gently resuspended in 1.4 mL of ice-cold Buffer A.

Step 6. The resuspended pellet from Step 5 is centrifuged in a tabletop microcentrifuge at 9750×g for 6 minutes at 4° C.

Step 7. The supernatant resulting from Step 6 is transferred from the conical microtubes to new conical microtubes.

Step 8. The pellet resulting from Step 7 is gently resuspended in ice-cold Buffer A, or in another buffer of choice, and centrifuged in a tabletop microcentrifuge at 9750×g for 6 minutes at 4° C.

Step 9. The pellet resulting from step 8 is frozen to −70° C., or is resuspended in another buffer of choice, for further analysis.

Example 3

Isolation of Intact Mitochondria from Non-Adherent Cells

Step 1. Non-adherent cells are rinsed in ice-cold (e.g., between about 0° C. and about 4° C.) 1× phosphate-buffered saline, and then centrifuged in a tabletop microcentrifuge at 600×g for 6 minutes at 4° C. The supernatant is removed, and the cell pellet is resuspended in 4 mL Buffer A (see Example 1) per 1×10$^7$ cells to produce a cell suspension.

Step 2. The cell suspension is centrifuged in a tabletop microcentrifuge in 1.5 mL conical microtubes (approximately 1 mL of cell suspension per microtube) at 600×g for 10 minutes at 4° C.

Step 3. The resulting supernatant from Step 2 is removed to new 1.5 mL conical microtubes and centrifuged in a tabletop microcentrifuge at 9750×g for 15 minutes at 4° C.

Step 4. The supernatant resulting from Step 3 is removed from the conical microtubes.

Step 5. The pellet resulting from Step 3 is gently resuspended in 1.4 mL of ice-cold Buffer A.

Step 6. The resuspended pellet from Step 5 is centrifuged in a tabletop microcentrifuge at 9750×g for 6 minutes at 4° C.

Step 7. The supernatant resulting from Step 6 is transferred from the conical microtubes to new conical microtubes.

Step 8. The pellet resulting from Step 7 is gently resuspended in ice-cold Buffer A, or in another buffer of choice, and centrifuged in a tabletop microcentrifuge at 9750×g for 6 minutes at 4° C.

Step 9. The pellet resulting from step 8 is frozen to −70° C., or is resuspended in another buffer of choice, for further analysis.

Example 4

Mouse liver: mice were anesthetized by inhalation of ~2% isoflurane (Abbott Animal Health, Abbott Park, Ill.). The abdomen is cut open by midline incision and the inferior vena cava and portal vein were exposed. To remove blood from the liver, heparin (10,000 USP units/mL (Baxter Healthservices); 150 µL in 200 µL of phosphate buffered saline (PBS) (calcium-free and magnesium-free)) was manually injected through the inferior vena cava with a 1 mL syringe and a 25-gauge one-inch (monoject 250) needle (Becton Dickinson, Franklin Lakes, N.J.) followed by cutting the portal vein. Subsequently, 15 mL of ice-cold PBS is injected through the same needle with a B-D 20 mL syringe (Becton Dickinson) at a speed of 3 mL/minute. The liver is excised, cleaned of extraneous tissues, and weighed. The entire liver is processed according to the procedures of Example 1.

Human liver: liver tissues obtained by needle biopsy or dissection are placed in ice-cold PBS and weighed. The samples are then processed according to the procedures of Example 1.

Example 5

Assessment of Mitochondria Isolation Protocols

Mitochondria are extracted from human HepG2 adherent cells as described above in Example 2 in triplicate. Mitochondria are also extracted using two publicly available mitochondria isolation kits: Kit T and Kit Q. Approximate isolation times for each protocol are provided in Table 1.

TABLE 1

Approximate time required to complete various mitochondria isolation protocols

| Isolation Protocol | Approximate Completion Time |
| --- | --- |
| Examples 1-3 | 30 minutes to 40 minutes |
| Kit T | 45 minutes to 60 minutes |
| Kit Q | 2 hours |

DNA is isolated from the mitochondrial extractions and analyzed using Invitrogen™ Qubit 4 Fluorometer, BioDrop, and quantitative PCR. Without being limited by any theory, the absorbance of a liquid sample can be measured (e.g., using an Invitrogen™ Qubit 4 Fluorometer or BioDrop) at specific wavelengths (e.g., 230 nm, 260 nm, 280 nm) to assess the purity of the sample for DNA, RNA, or individual nucleotides. DNA, RNA, and individual nucleotides all absorb at 260 nm. Typically, the ratio of absorbance at 260 nm and 280 nm ("A260/A280") is used to assess the purity of a sample for DNA or RNA. An A260/A280 ratio of approximately 1.8 is generally accepted as "pure" for a DNA sample; an A260/A280 ratio of approximately 2.0 is generally accepted as "pure" for an RNA sample. If a sample's A260/A280 ratio is considerably lower it may indicate that contaminants, such as protein or phenol, are present in the sample. The ratio of absorbance of at 260 nm and 230 nm ("A260/A230") can also be used to assess the purity of a nucleic acid sample. A "pure" sample typically has a higher A260/A230 ratio as compared to its A260/A280 ratios; A260/A230 ratios for "pure" samples typically range from 2.0-2.2.

Table 2 provides the quantity and quality of isolated DNA from each isolation protocol as measured using an Invitrogen™ Qubit 4 and BioDrop DUO+. Within each Set, the same number of starting cells (from the same cell line and cell culture) are harvested at the same time for use in each isolation protocol.

TABLE 2

Mitochondria Isolation Quantities and Quality Readings. Quantity is measured using Invitrogen ™ Qubit 4; Absorbance ratios are measured using BioDrop DUO+. Each measurement is from one sample.

| Isolation Protocol | Total Quantity Isolated (µg) | A260/A230 Ratio | A260/A280 Ratio |
| --- | --- | --- | --- |
| Set 1 (Approximately 1 × $10^7$ cells/sample) | | | |
| Example 2 | 3.768 | 2.131 | 1.955 |
| Kit T | 0.235 | 0.854 | 1.875 |
| Kit Q | 1.139 | 1.822 | 1.875 |
| Set 2 (Approximately 2 × $10^7$ cells/sample) | | | |
| Example 2 | 11.40 | 2.503 | 2.061 |
| Kit T | 3.015 | 1.925 | 2.072 |
| Kit Q | 5.865 | 2.155 | 1.919 |

Isolated mitochondrial fractions are also examined using transmission electron microscopy. The fraction isolated with Kit T contained very few intact mitochondria. Almost all of the mitochondria observed were broken and swollen mitochondria that retained only their outer membrane and no cristae. The fraction isolated with Kit T also exhibited high levels of contamination with broken nuclei and swollen rough endoplasmic reticulum (ER). See FIG. 1A and FIG. 1B.

The mitochondrial fraction isolated with Kit Q contained fewer broken mitochondria as compared to the fraction isolated with Kit T. However, the mitochondrial fraction isolated with Kit Q still contained many broken mitochondria. Contamination with swollen rough ER was also observed. See FIG. 2A and FIG. 2B.

The mitochondrial fraction isolated with the instant mitochondrial isolation protocol used in Examples 1-3 showed the greatest amount of intact mitochondria amongst the three tested protocols. Notably, the density of intact mitochondria using the instant mitochondria isolation protocols was much higher than in Kit Q and Kit T isolations. The instant mitochondrial isolation protocol also showed less contamination with swollen rough ER as compared to the isolations from Kit Q and Kit T. See FIG. 3A and FIG. 3B.

DNA is isolated from the isolated mitochondria. The isolated DNA is then used for quantitative PCR (qPCR) to further quantify the amount of mitochondrial DNA present in each sample. See Table 3. Actin (GenBank Accession No. NG_007992; "Actin" in Table 3), encoded by the nuclear genome, and a mitochondrial tRNA gene (GenBank Accession No. NC_012920.1; nucleotides 3216-3318; "mt tRNA" in Table 3), are tested. Without being limited by any theory, qPCR allows for the quantification of the amount of starting DNA in a sample. In qPCR, amplified DNA is fluorescently labeled, and the amount of fluorescence released during each amplification cycle is directly proportional to the amount of amplified DNA. The higher the starting amount of a given DNA molecule in a sample, the faster the fluorescence will increase, and the earlier fluorescence will be detected in the sample. Essentially, the more copies of a target DNA segment there are in a sample, the earlier (e.g., lower PCR cycle) fluorescence will be detected. The first cycle in which fluorescence is detected is termed the detection threshold (Ct).

TABLE 3 qPCR of isolated mitochondrial DNA

| Isolation Protocol/Gene | Set 1 | | Set 2 | |
|---|---|---|---|---|
| | Ct Mean | Delta Ct | Ct Mean | Delta Ct |
| Example 2 -Actin | 17.2 | 4.2 | 22 | 9.3 |
| Example 2 - mt tRNA | 13.0 | | 12.7 | |
| Kit T -Actin | 24.5 | 4.4 | 21 | 6 |
| Kit T - mt tRNA | 20.1 | | 15 | |
| Kit Q-Actin | 17.8 | 3.8 | 20 | 10 |
| Kit Q - mt tRNA | 14 | | 10 | |

The invention claimed is:

1. A method for isolating intact mitochondria from a population of cells comprising:
   (a) suspending said population of cells in an ice-cold buffer of about pH 7.4 comprising:
      (i) about 250 mM sucrose;
      (ii) about 5 mM magnesium chloride ($MgCl_2$); and
      (iii) about 10 mM 2-Amino-2-(hydroxymethyl)-1,3-propanediol hydrochloride (Tris-HCl)
      to generate a cell suspension;
   (b) centrifuging said cell suspension at about 600× g for about 10 minutes at about 4 degree C. to generate a supernatant;
   (c) centrifuging said supernatant to generate a first mitochondria-rich pellet;
   (d) resuspending said first mitochondria-rich pellet in said buffer to generate a first mitochondrial suspension;
   (e) centrifuging said first mitochondrial suspension to generate a second mitochondria-rich pellet;
   (f) resuspending said second mitochondria-rich pellet in said buffer to generate a second mitochondrial suspension;
   (g) centrifuging said second mitochondrial suspension to generate a third mitochondria-rich pellet; and
   (h) resuspending said third mitochondria-rich pellet in said buffer to generate a third mitochondrial suspension,
   wherein the centrifuging steps (c), (e), and (g) are performed at about 4 degree C. at a relative centrifugal force of between about 9,250× g and about 9,800× g, and
   wherein resulting said third mitochondrial suspension comprises a DNA purity of greater than or equal to 70%.

2. A method for isolating intact mitochondria from a tissue comprising:
   (a) generating a mashed tissue;
   (b) suspending said mashed tissue in an ice-cold buffer of about pH 7.4 comprising:
      (i) about 250 mM sucrose;
      (ii) about 5 mM magnesium chloride ($MgCl_2$); and
      (iii) about 10 mM 2-Amino-2-(hydroxymethyl)-1,3-propanediol hydrochloride (Tris-HCl)
      to generate a cell suspension;
   (c) centrifuging said cell suspension at about 600× g for about 10 minutes at about 4 degree C. to generate a supernatant;
   (d) centrifuging said supernatant to generate a first mitochondria-rich pellet;
   (e) resuspending said first mitochondria-rich pellet in said buffer to generate a first mitochondrial suspension,
   (f) centrifuging said first mitochondrial suspension to generate a second mitochondria-rich pellet;
   (g) resuspending said second mitochondria-rich pellet in said buffer to generate a second mitochondrial suspension;
   (h) centrifuging said second mitochondrial suspension to generate a third mitochondria-rich pellet; and
   (i) resuspending said third mitochondria-rich pellet in said buffer to generate a third mitochondrial suspension,
   wherein the centrifuging steps (d), (f), and (h) are performed at about 4 degree C. at a relative centrifugal force of between about 9,250× g and about 9,800× g, and
   wherein resulting said third mitochondrial suspension comprises a DNA purity of greater than or equal to 70%.

3. The method of claim 1, wherein said population of cells comprises a population of adherent cells or a population of non-adherent cells.

4. The method of claim 1, wherein said first mitochondrial suspension is substantially free of non-mitochondrial cellular components.

5. The method of claim 1, wherein said second mitochondrial suspension, said third mitochondrial suspension, or both, is substantially free of non-mitochondrial cellular components.

6. The method of claim 2, wherein said second mitochondrial suspension, said third mitochondrial suspension, or both is substantially free of non-mitochondrial cellular components.

7. The method of claim 1, wherein said third mitochondrial suspension comprises a protein purity of greater than or equal to 70%.

8. The method of claim 1, wherein said third mitochondrial suspension comprises a ratio of mitochondrial structural protein to nuclear structural protein of at least 9:1.

9. The method of claim 8, wherein
   (a) said mitochondrial structural protein is selected from the group consisting of fatty-acyl-CoA synthase, carnitine acyl transferase, TOM complex, carnitine acetyltransferase, NADH/ubiquinone oxidoreductase, ubiquinone, cytochrome c reductase, cytochrome c oxidase, succinate dehydrogenase, and mitochondrial ATP synthase; and
   (b) said nuclear structural protein is selected from the group consisting of lamin A, lamin B1, lamin B2, NuMA, lamin C, nesprin, emerin, lamina-associated protein1 (LAP1), LAP2, lamin B receptor (LBR), nurim, MAN1, Barrier to Autointegration Factor (BAF), and Heterochromatin Protein1 (HP1).

10. The method of claim 1, wherein said buffer comprises at least one DNase inhibitor, at least one RNase inhibitor, or both.

11. The method of claim 2, wherein said buffer comprises at least one DNase inhibitor, at least one RNase inhibitor, or both.

12. The method of claim 1, wherein said population of cells is selected form the group of a population of mammal cells, a population of fish cells, a population of reptile cells, a population of amphibian cells, a population of avian cells, a population of insect cells, a population of plant cells, and a population of fungal cells.

13. The method of claim 2, wherein said tissue is selected from the group consisting of a mammal tissue, a fish tissue, a reptile tissue, an amphibian tissue, an avian tissue, an insect tissue, and a plant tissue.

14. The method of claim 2, wherein said first mitochondrial suspension is substantially free of non-mitochondrial cellular components.

15. The method of claim 2, wherein said third mitochondrial suspension comprises a protein purity of greater than or equal to 70%.

16. The method of claim 2, wherein said third mitochondrial suspension comprises a ratio of mitochondrial structural protein to nuclear structural protein of at least 9:1.

17. The method of claim 16, wherein
  (a) said mitochondrial structural protein is selected from the group consisting of fatty-acyl-CoA synthase, carnitine acyl transferase, TOM complex, carnitine acetyltransferase, NADH/ubiquinone oxidoreductase, ubiquinone, cytochrome c reductase, cytochrome c oxidase, succinate dehydrogenase, and mitochondrial ATP synthase; and
  (b) said nuclear structural protein is selected from the group consisting of lamin A, lamin B1, lamin B2, NuMA, lamin C, nesprin, emerin, lamina-associated protein1 (LAP1), LAP2, lamin B receptor (LBR), nurim, MAN1, Barrier to Autointegration Factor (BAF), and Heterochromatin Proteinl (HP1).

\* \* \* \* \*